United States Patent [19]

Umemura et al.

[11] Patent Number: 5,523,058
[45] Date of Patent: Jun. 4, 1996

[54] ULTRASONIC IRRADIATION APPARATUS AND PROCESSING APPARATUS BASED THEREON

[75] Inventors: Shinichiro Umemura, Hachioji; Kenichi Kawabata, Hiki-gun; Kenko Uchida, Hiki-gun; Kenji Yasuda, Hiki-gun; Yasuo Wada, Tokyo; Atsushi Hiraiwa, Higashimurayama, all of Japan

[73] Assignee: Hitachi, Ltd., Tokyo, Japan

[21] Appl. No.: 240,733

[22] PCT Filed: Sep. 14, 1993

[86] PCT No.: PCT/JP93/01310

§ 371 Date: May 12, 1994

§ 102(e) Date: May 12, 1994

[87] PCT Pub. No.: WO94/06380

PCT Pub. Date: Mar. 31, 1994

[30] Foreign Application Priority Data

Sep. 16, 1992 [JP] Japan .................................. 4-246179

[51] Int. Cl.⁶ .............................. B01F 11/02; A61B 8/00; B06B 1/00
[52] U.S. Cl. .................... 422/128; 128/660.01; 134/1; 310/322; 366/116; 366/127; 422/20
[58] Field of Search ............... 422/20, 128, 224; 134/1; 366/108, 114, 116, 127; 128/660.01, 660.03, 661.08; 310/320, 322, 334

[56] References Cited

U.S. PATENT DOCUMENTS

| | | | |
|---|---|---|---|
| 3,117,768 | 1/1964 | Carlin | 366/114 |
| 3,805,596 | 4/1974 | Klahr | 73/602 |
| 4,168,295 | 9/1979 | Sawyer | 366/114 X |
| 4,249,146 | 2/1981 | Yen et al. | 333/195 |
| 4,556,467 | 12/1985 | Kuhn et al. | 366/127 X |
| 4,836,684 | 6/1989 | Javorik et al. | 366/114 |
| 5,065,066 | 11/1991 | Nakatani et al. | 310/320 |
| 5,076,854 | 12/1991 | Honda et al. | 134/25.1 X |
| 5,158,071 | 10/1992 | Umemura et al. | 128/660.03 |
| 5,259,384 | 11/1993 | Kaufman et al. | 128/660.01 |

FOREIGN PATENT DOCUMENTS 2-126848 5/1990 Japan.

*Primary Examiner*—Timothy M. McMahon
*Assistant Examiner*—Robert Carpenter
*Attorney, Agent, or Firm*—Antonelli, Terry, Stout & Kraus

[57] ABSTRACT

By providing an ultrasonic irradiation apparatus for generating acoustic cavitation efficiently, it is intended to realize an ultrasonic therapeutic apparatus for generating the action of cavitation on a living body suitable for medical treatment of malignant tumors and medical treatment of thrombi and calculi, an ultrasonic diagnostic apparatus for generating cavitation for emphasizing an ultrasonic echo image such as a blood flow and utilizing the reflection capability of the cavitation, an ultrasonic chemical reaction accelerating apparatus, an ultrasonic cleaning apparatus or an ultrasonic sterilizing apparatus. Irradiation focus/code signals for defining irradiated acoustic fields of a fundamental wave and a second harmonic wave as well as focus positions/acoustic pressure distribution forms of the respective waves are applied from an irradiation unit main control circuit to drive phase generating circuits. Generated drive phases are applied to drive signal generating circuits, generated drive signals are applied to element drive circuits and a group of fundamental frequency elements and a group of second harmonic elements are driven. The drive phases are controlled such that the fundamental wave and second harmonic wave are superimposed on each other in a medium near a focal point, thus generating acoustic cavitation locally and efficiently.

24 Claims, 23 Drawing Sheets

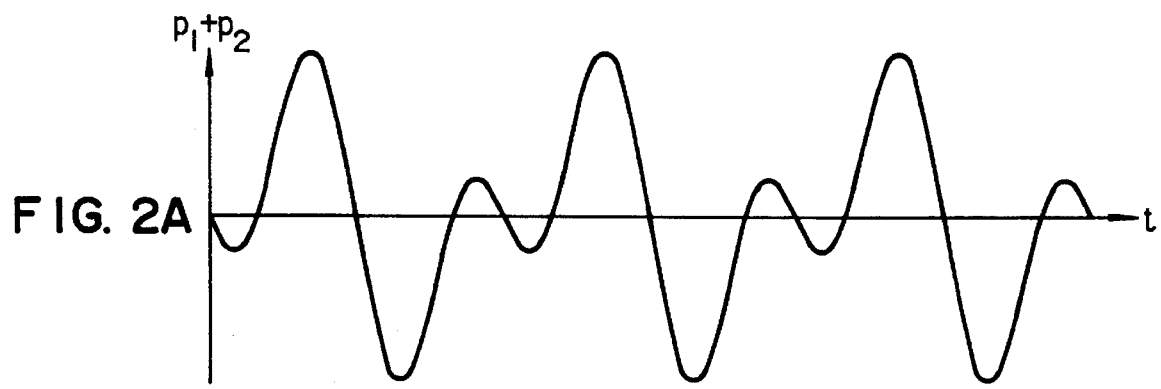
FIG. 2A
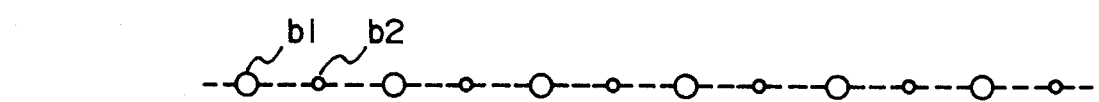
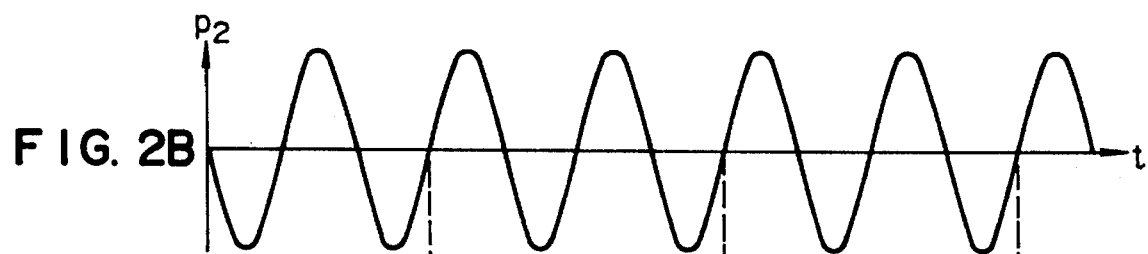
FIG. 2B
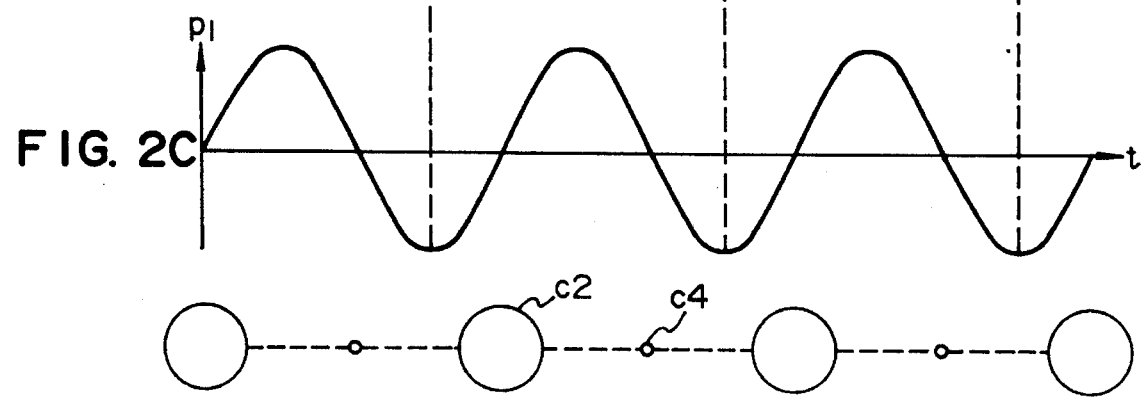
FIG. 2C

F I G. 7
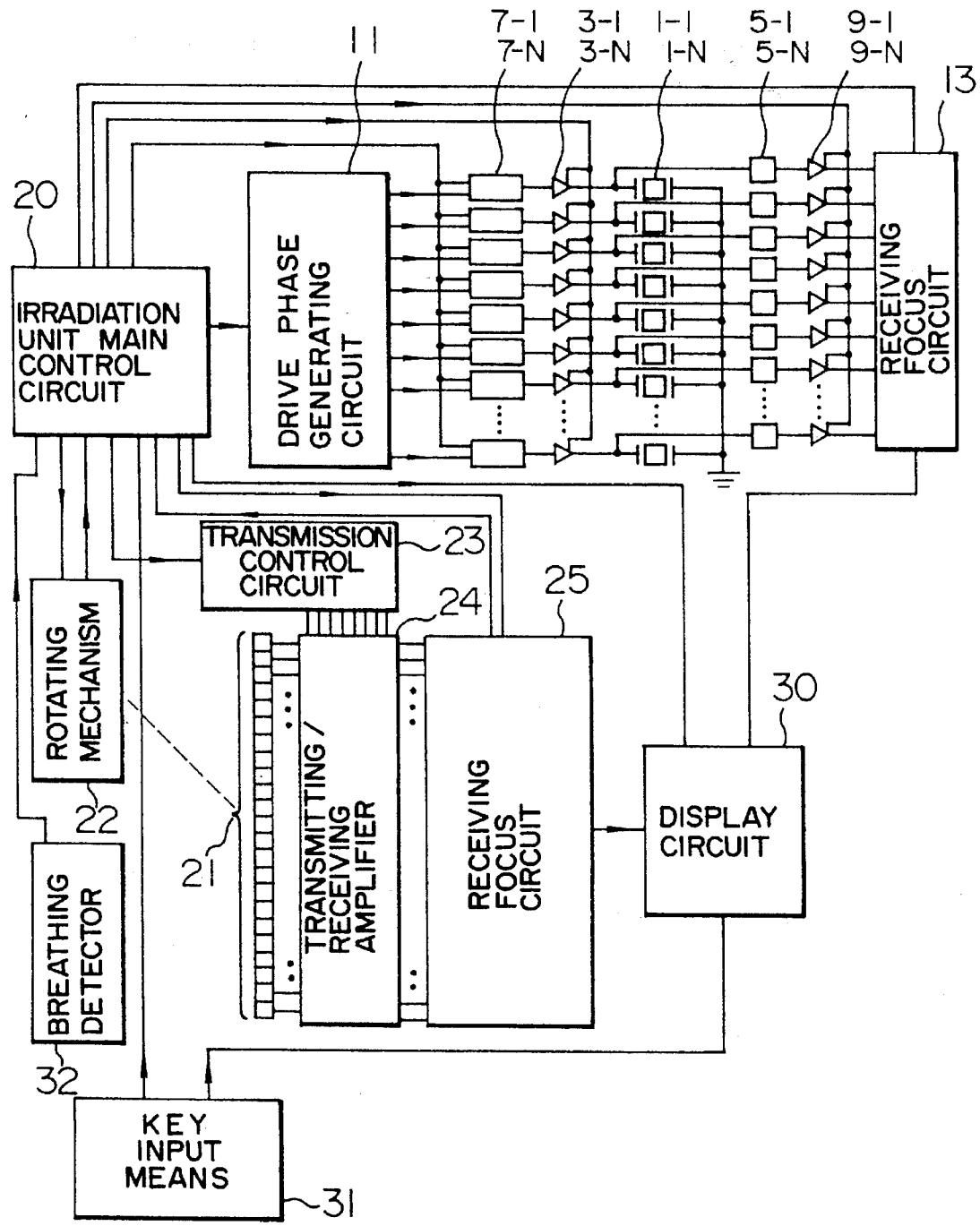

$\alpha : 1-\alpha$ $\beta : 1-\beta$ $$\frac{\gamma}{2} : 1-\gamma : \frac{\gamma}{2}$$

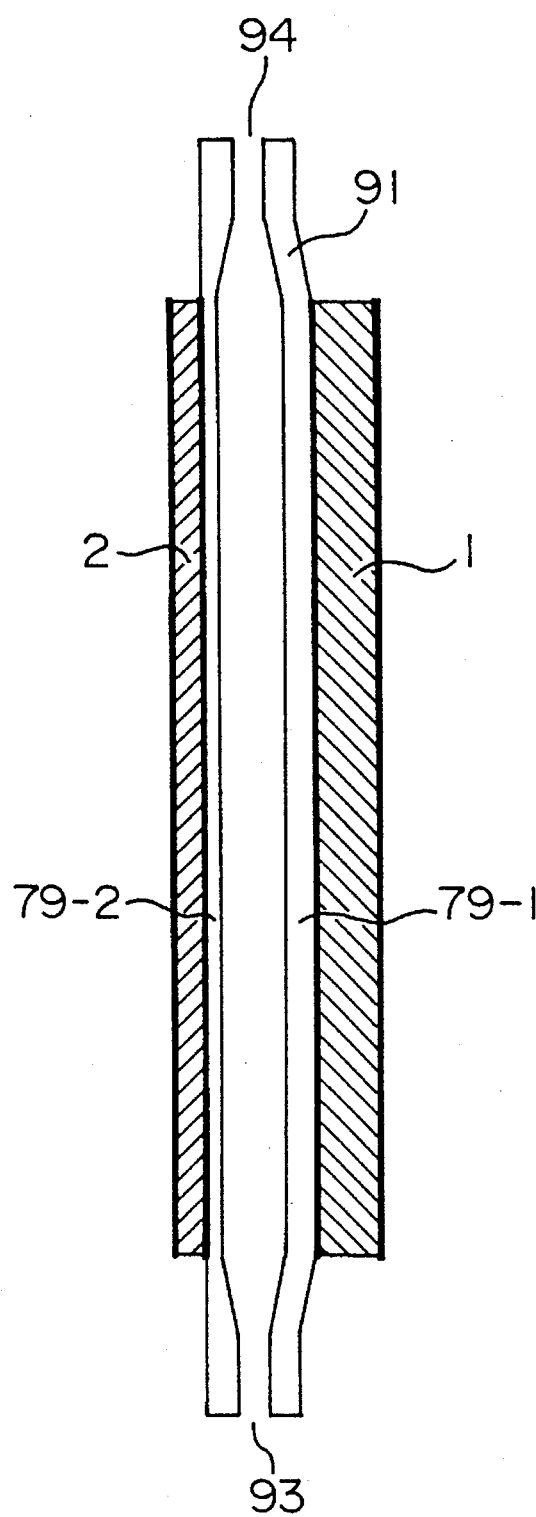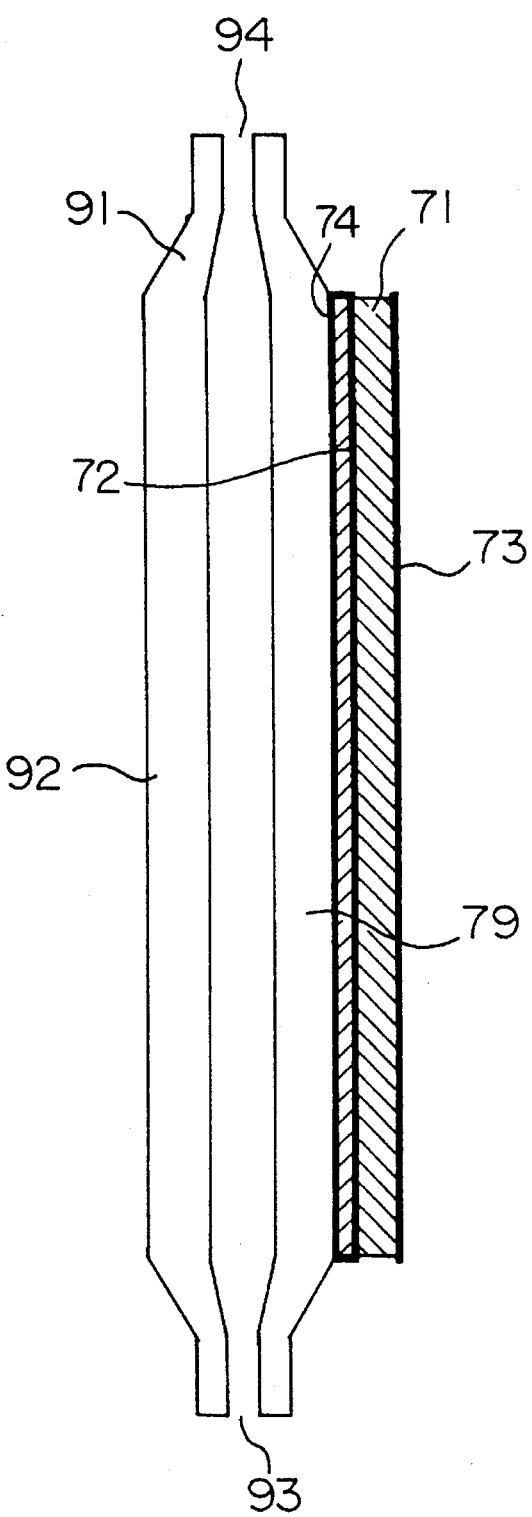

α WHEN THE FUNDAMENTAL FREQUENCY
WAVE AND SECOND HARMONIC WAVE ARE
REPRESENTED BY SIN(2πf) AND SIN(4πf+α)

5,523,058

ULTRASONIC IRRADIATION APPARATUS AND PROCESSING APPARATUS BASED THEREON

FIELD OF THE INVENTION

The present invention relates to an ultrasonic therapeutic apparatus suitable for medical treatment of malignant tumors and medical treatment of thrombi and calculi, an ultrasonic diagnostic apparatus having the function of generating ultrasonic cavitation for emphasizing an ultrasonic echo image of, for example, blood flow, an ultrasonic apparatus for accelerating chemical reactions, an ultrasonic cleaning apparatus for solid surfaces, an ultrasonic bubble generating apparatus or a sterilizing apparatus for liquid.

DESCRIPTION OF RELATED ART

A medical treatment of malignant tumors and a remedy for calculi which are based on irradiation of a converging high-intensity acoustic wave have been expected to serve as a noninvasive modality which does not depend on an operation and as a modality which makes much of the quality of life after an operation on a patient and increase their social value more and more in the future, too. Acoustic cavitation is considered to play an important role in generating the effect of medical treatment based on high-intensity focused acoustic wave irradiation. It has also been known that acoustic cavitation plays an important role also in accelerating chemical reactions and in cleaning based on ultrasound irradiation.

As a method of efficiently inducing the generation and collapse under pressure of acoustic cavitation for the above purposes, a technique has hitherto been reported as proposed in JP-A-2-126848, according to which ultrasonic waves are irradiated by switching acoustic fields at intervals of 1 to 100 msec. In this technique, based on the fact that the ultrasonic irradiation time, 1 to 100 msec, is needed for generation of acoustic cavitation, ultrasonic irradiation is carried out while switching acoustic fields of different wave fronts at intervals of the above time range whereby the cycle of generation of acoustic cavitation by one acoustic field and collapse under pressure of the acoustic cavitation by the other acoustic field is repeated. Through this, the efficiency of ultrasonic chemical reaction can be improved by an order of magnitude for the same ultrasonic power in comparison with the case without the switching of acoustic fields.

In a semiconductor device production process, high-density integration of devices prevails and concomitantly therewith, deposition of minute foreign matter on substrates or surface contamination affect the yield of products to a great extent. Therefore, the cleaning process becomes very important in the semiconductor device production process. When ultrasound is irradiated in a liquid containing a minute amount of gas, pressure increase and pressure reduction due to the ultrasound, which are waves of condensation and rarefaction, are caused in a local region, bubbles of a size corresponding to a frequency of the ultrasound are vibrated, and collapse under pressure of bubbles occurs because of a phenomenon called acoustic cavitation. It has been known that the cleaning effects are observed under the condition that acoustic cavitation takes place and by virtue of this characteristic, the acoustic cavitation phenomenon is widely used for cleaning processes; cleaning of semiconductor substrates, glasses or tableware.

Since the ultrasound changes its cleaning effect in accordance with the form of its irradiation, a variety of methods for improving the efficiency of cleaning by arranging the location where a portion is irradiated with ultrasound have been devised. However, such arrangements could not improve the cleaning efficiency sufficiently. For more efficient cleaning, a method is needed which can efficiently generate acoustic cavitation serving as a source of cleaning. As a conventional example in which an irradiation source of ultrasound is contrived in an ultrasonic cleaning apparatus, a cleaning apparatus as disclosed in JP-A-2-157078 has been devised which has a higher cleaning power than the case of ultrasound of a single frequency by having a source for generating ultrasonic waves of a plurality of frequencies. In this example, the additive effect of the ultrasonic waves irradiated from the respective ultrasound sources can be attained but the cleaning effect is limited because a combination of frequencies was not so set as to generate acoustic cavitation efficiently.

Conventionally, in sterilization of liquid, a method using chlorine or ultraviolet rays has been used widely. In the case that the composition of liquid may be changed, especially, in the case of waste liquid disposal, chlorine treatment is used and in order to perform sterilization which does not change the composition of liquid to a great extent, ultraviolet rays are used.

Sterilization using chlorine has been practiced for a relatively long time, but it changes the composition of a liquid to be processed and so requires operations such as neutralization and removal of remaining chlorine to allow the sterilized liquid to be used for another purpose, raising problems from the standpoint of safety and environmental cost. Sterilization using ultraviolet rays does not use any chemicals, and so it is used widely as a sterilization method which is simple and makes easy the handling of liquid after sterilization. However, since most organic compounds have a large absorption coefficient for ultraviolet rays, ultraviolet rays are not expected to be effective for a liquid containing a large amount of organic compounds unless the liquid is located near a light source. It has been known that when an ultrasound is irradiated in a liquid, acoustic cavitation occurs and sterilization can be induced thereby.

SUMMARY OF INVENTION

However, when taking the application to medical treatment, for a particular example, there are so many different situations in real clinical applications even with the above-described techniques, ultrasonic power necessary for obtaining sufficient therapeutic effects is not always of a sufficiently small level from the standpoint of the potential side effects due to the ultrasound. On the other hand, even in the conventional techniques improved as described previously, only a very small part of irradiated ultrasonic energy is converted into the energy effective for generation and collapse under pressure of acoustic cavitation and in this respect, there still remains a possibility of improving the efficiency in principle. Accordingly, there is possibility of having a technique which can afford to obtain the same therapeutic effect by a smaller ultrasonic power level than that of the aforementioned conventional techniques and its realization has been desired strongly for the sake of carrying out medical treatment while suppressing side effects as much as possible.

In the light of the aforementioned social demands and potential technical possibilities, it is an object of the present invention to provide an ultrasonic irradiation technique for generating acoustic cavitation with a significantly higher efficiency than the conventional techniques. Based on this, a concrete object is to provide an ultrasonic therapeutic apparatus which can essentially eliminate side effects, or a highly efficient ultrasonic chemical reaction accelerating apparatus, ultrasonic cleaning apparatus or ultrasonic sterilizing apparatus. In addition, it is also intended to provide the ultrasonic therapeutic apparatus with the function of preventing erroneous irradiation by visualizing the efficiently generated acoustic cavitation as an ultrasonic image or to improve the imaging capability of an ultrasonic diagnostic apparatus by emphasizing an echo characteristic of, for example, a blood flow.

In connection with the ultrasonic cleaning apparatus, an object of the present invention is to provide a cleaning apparatus with an ultrasound source at a plurality of frequencies which has higher cleaning capability than the case of a single frequency and also provide higher cleaning effects as a result of the synergistic effect of the plural frequencies by setting a combination of the frequencies for efficient generation of acoustic cavitation.

Since the size of bubbles participating in acoustic cavitation is essentially inversely proportional to the ultrasound frequency, large bubbles collapse under pressure when a low frequency is used. With an increase in density of integration, the size of a pattern in a semiconductor device decreases and when an ultrasound wave at a low frequency of, for example, 20 kHz is used for cleaning, the size of a bubble generated by acoustic cavitation approximates that of a pattern formed on a semiconductor device, bringing about such a potential adverse influence that a bubble enters a groove of the pattern in the semiconductor device and will not go out of the groove. Therefore, a high ultrasound frequency must be used but there arises a problem that acoustic cavitation effective for cleaning is not apt to be generated at a higher frequency. An object of the present invention is to provide a cleaning apparatus which has higher cleaning capability than the conventional apparatus by generating acoustic cavitation effective for cleaning even at a high frequency of, especially, 500 kHz or higher employing an ultrasonic irradiation method which induces highly efficient generation of acoustic cavitation which is a source of cleaning. The aforementioned collapse under pressure of a bubble due to acoustic cavitation leads to generation of a local region of high pressure and high temperature under a pacified condition, but in the conventional ultrasonic cleaning apparatus, only the mechanical effects of the acoustic cavitation are utilized and there is no example of a cleaning apparatus utilizing the chemical effects of the acoustic cavitation. The cleaning effect of ultrasound is classified into one based on mechanical effects and the other based on chemical effects. In ordinary ultrasonic cleaning at a low frequency, the mechanical effect is dominant. Cleaning with ammonia and hydrogen peroxide or hydrogen peroxide and sulfuric acid in the process of semiconductor devices includes a chemical process of oxidizing the surface of a semiconductor device or a substance deposited on the surface of the semiconductor device. The present invention intends to obtain sufficient cleaning effects in connection with such chemical cleaning.

When ultrasound is used for sterilization of liquid, the problem that the effect can be attained only near a generating source can be avoided in contrast to the case of ultraviolet rays. Also, since the composition of liquid is less changed by the treatment than in the case of using chlorine, liquid after sterilization can be used without being subjected to a post-treatment. While in the conventional ultrasonic irradiation method acoustic cavitation inducing a sufficient sterilization effect cannot be generated and consequently sterilization due to ultrasound is hardly carried out, the present invention uses an ultrasonic irradiation method suitable for generating acoustic cavitation with the aim of providing a sterilizing apparatus having sufficient sterilization effects in comparison with sterilization using chlorine or ultraviolet rays.

BRIEF DESCRIPTION OF THE DRAWINGS

FIG. 2A is a diagram showing a resultant superimposed waveform obtained by superimposing a waveform p1 at the fundamental frequency $\sin(2\pi ft)$, and a waveform p2 at the second harmonic frequency $-\sin(4\pi ft)$.

FIG. 2B schematically shows the waveform p2 of the second harmonic wave and behavior of the generated bubbles are shown on upper and lower sides of that waveform.

FIG. 2C is a diagram schematically showing the waveform p1 of the fundamental wave and behavior of bubbles which are generated on upper and lower sides of that waveform p1 by the waveform p2 of the second harmonic wave and grow further.

FIG. 7 is a block diagram showing the configuration of another embodiment of the ultrasonic irradiation apparatus according to the present invention.

FIG. 23 is a diagram showing an example of the configuration of a reactor of an ultrasonic chemical reaction apparatus according to the present invention.

FIG. 24 is a diagram showing another example of the reactor of the ultrasonic chemical reaction apparatus according to the present invention.

DESCRIPTION OF THE PREFERRED EMBODIMENTS

It has been known that when a sinusoidal ultrasound wave with a relatively high intensity propagates in a medium such as a living body or a liquid, its pressure waveform changes from a sine wave to a so-called N-wave (a wave in which the rise of pressure is more rapid than the fall of pressure) as the propagation proceeds. This is due to a non-linear property of the medium wherein as the pressure in the medium increases, the acoustic speed increases, and in the case of pulsed ultrasound, it has been known that the pressure waveform changes to a waveform having a larger positive peak pressure than a negative peak pressure as the propagation proceeds. On the other hand, it has been known that acoustic cavitation is unlikely to be generated in an acoustic field called a transmission mode or a propagation mode in which high-intensity reflectors do not exist but is likely to be generated in an ultrasonic acoustic field in which high-intensity reflectors do exist. The above can be explained by considering that the wave in which the fall of pressure generated by propagation of ultrasound is more gradual than the rise of pressure or the negative peak pressure is smaller than the positive peak pressure are disadvantageous to the generation of acoustic cavitation but the waveform becomes advantageous to the generation of acoustic cavitation when phase inversion at a reflector takes place.

Figure 1:
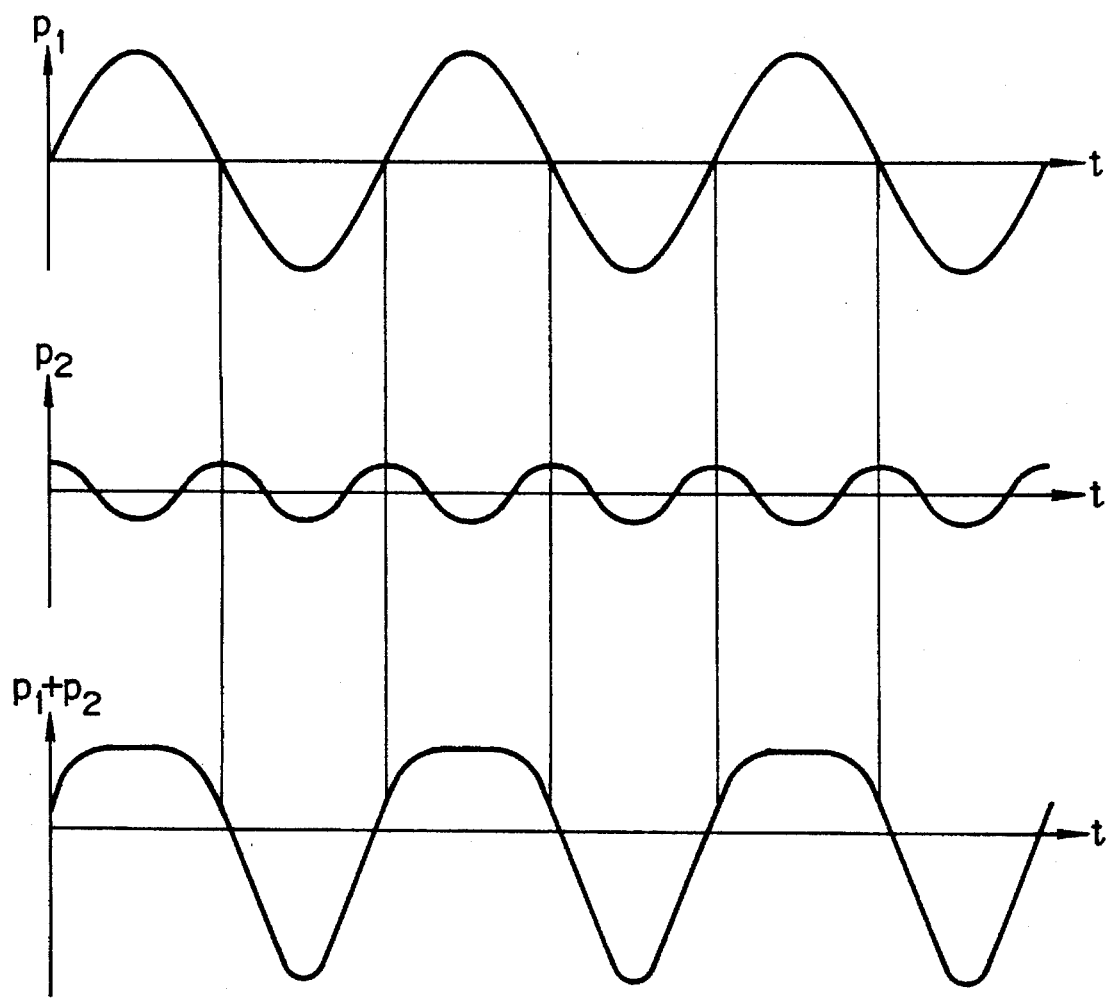
FIG. 1 is a diagram showing an example of a fundamental wave, a second harmonic wave, and a superimposed wave obtained by superimposing these two waves.

Based on the above consideration, the present invention proposes that ultrasound considered to be generated as a result of phase inversion in the above case and having a waveform advantageous to the acoustic cavitation generation can be obtained through synthesis without resort to any reflectors by causing ultrasound of a fundamental frequency to be added to ultrasound having a frequency which is twice the fundamental frequency at an object to be irradiated. More particularly, as shown in, for example, FIG. 1, by adding to ultrasound p1 of a fundamental frequency ultrasound p2 having a frequency which is twice the fundamental frequency in a suitable phase relationship, ultrasound p1+p2 which has a waveform advantageous to the generation of acoustic cavitation and having a larger negative pressure peak than a positive pressure peak can be synthesized.

A wave transmitter may be so configured that the fundamental wave p1 and the second harmonic wave p2 are generated simultaneously from the same wave transmitter element or alternatively they are generated from separate wave transmitter elements and are synthesized at substantially the same focal point. A first embodiment proposes that an array type wave transmitter is used which is so configured that a fundamental wave p1 and a second harmonic wave p2, which are able to generate acoustic cavitation in a region more limited to the vicinity of a focal point, are generated from a plurality of wave transmitter elements, respectively, whereby a focal point of the fundamental wave p1 and a focal point of the second harmonic wave p2 are superimposed on each other while they are electronically scanned simultaneously.

This embodiment also proposes that in order to allow a position of the acoustic cavitation generation to be monitored in the form of a position in an ultrasonic echo image, an ultrasonic echo image of an irradiated object is formed simultaneously by transmitting and receiving a pulse wave of a higher frequency than the second harmonic wave.

A second embodiment proposes an example in which simultaneous generation of the fundamental frequency wave p1 and second harmonic wave p2 from the same wave transmitter element is contrived.

A third embodiment proposes that a plane wave at the fundamental frequency and a plane wave at a frequency which is twice the fundamental frequency are added together so that wave fronts of the two frequencies are rendered to be substantially parallel to each other and the plane waves are irradiated on the same object at the same time.

A fourth embodiment proposes effective utilization of the aforementioned acoustic cavitation generation in a chemical process such as oxidizing the surface of a semiconductor device or substances deposited on the surface of a semiconductor device, for example, cleaning using ammonia and hydrogen peroxide or hydrogen peroxide and sulfuric acid, in the process of semiconductor device production.

A fifth embodiment proposes an application to sterilization of liquid.

A concrete example of the synthesis of ultrasound of the fundamental wave p1 and ultrasound of the second harmonic wave p2 which can generate acoustic cavitation efficiently at an irradiated object in these embodiments will first be explained.

FIGS. 2A and 2B show a acoustic pressure waveform obtained when the phase relation is set such that an ultrasound waveform a p1 of a fundamental frequency f is represented by $\sin(2\pi ft)$ with respect to time t and a second harmonic waveform p2 is approximated by $-\sin(4\pi ft)$, demonstrating an example in which the fall of a synthesized acoustic pressure is steeper than the rise thereof to act on the generation of acoustic cavitation very advantageously. Taking this case as an example, the generation and function of acoustic cavitation will be described with the aid of diagrams.

FIG. 2A is a diagram showing a waveform resulting from synthesis of the fundamental frequency waveform p1 of $\sin(2\pi ft)$ and the second harmonic waveform p2 of $-\sin(4\pi ft)$. FIG. 2B diagrammatically shows the second harmonic waveform p2 and the behavior of bubbles which are generated and grow on the upper and lower sides of the waveform p2. FIG. 2C diagrammatically shows the fundamental waveform p1 and the behavior of the bubbles generated and caused to grow by the second harmonic waveform p2, which further grow on the upper and lower sides of the waveform p1.

Firstly, the generation of acoustic cavitation is started by the second harmonic wave p2 ($=-\sin(4\pi ft)$). Since the radius of a resonant bubble due to the second harmonic wave is small amounting to a half of the radius of a resonant bubble due to the fundamental wave p1 ($=\sin(2\pi ft)$), the initiation of acoustic cavitation effected using the second harmonic wave is significantly advantageous over that effected using only the fundamental wave p1. In that case, the radius of a cavitation bubble vibrates at the period of the second harmonic wave but in the initial phase of the generation of the bubble, the bubble radius is smaller than the resonant bubble radius and has a maximum (for example, b1) at a negative pressure peak of the second harmonic wave and a minimum (for example, b2) at a positive pressure peak as shown at an upper part in FIG. 2B. In other words, enlargement and reduction are repeated within a size range of from b2 to b1.

When cavitation bubbles grow by receiving energy of the second harmonic wave p2 and the radius of a cavitation bubble grows to approximately the radius of a resonant bubble due to the second harmonic wave, the phase of vibration of the bubble radius is delayed by 90° and the bubble radius has a maximum (for example, b3) at a zero-crossing point from negative pressure to positive pressure. A bubble corresponding to positive pressure (for example, b4) remains essentially identical to a bubble in the phase of non-resonance.

In this case, with the superimposition of the fundamental wave p1 effected in the above-described phase relation, the timings for maximizing the vibration of the bubble radius in the second harmonic wave coincide with a timing of a negative pressure peak of the fundamental wave once every two periods of the second harmonic wave (for example, c1) and as a result, the cavitation bubble further grows by receiving energy of the fundamental wave, reaching at least the size (for example, c2) of a resonant bubble due to the fundamental wave. Even for the fundamental wave, a bubble corresponding to positive pressure remains essentially identical to a bubble corresponding to positive pressure in the initial phase in the second harmonic wave (for example, c3 and c4) regardless of the resonance and non-resonance phases.

When a grown bubble collapses under pressure, an internal gas is adiabatically compressed to generate energy locally. In order for the energy to be sufficient for the purpose of triggering a chemical reaction, the bubble subject to collapse under pressure must be at least larger than a certain size. By selecting a fundamental frequency which is somewhat low, the size of a resonant bubble at the fundamental frequency can be set to the necessary size or larger. In the case where the fundamental frequency alone is irradiated, however, there arises a problem that the cavitation generation cannot be started successfully if the resonant bubble due to the fundamental wave is too large. Contrarily, by effecting the superimposition of the second harmonic wave in a suitable phase relation by using the method of the present invention, each of the initiation of the cavitation generation and the growth of the cavitation bubble to a sufficient size can be accomplished efficiently through the cooperation of the second harmonic wave with the fundamental wave.

In addition, when an ultrasonic imaging unit is used which transmits/receives a pulse wave of a frequency higher than that of the second harmonic wave to form an ultrasonic echo image of an irradiated object, monitoring with self-matching capability due to wave motion having a speed essentially equal to that of the ultrasound which exerts acoustic cavitation on an irradiated object will be possible and therefore monitoring relatively immune to the influence of a acoustic speed distribution of an intermediate medium can be realized. Further, by configuring the ultrasonic imaging unit to enable it to receive a frequency component of an even multiple of the second harmonic ultrasound which exerts acoustic cavitation on an irradiated object, a position where acoustic cavitation is generated or a position where acoustic cavitation is highly likely to be generated can be displayed while being superimposed on an ultrasonic echo image.

The first embodiment of the present invention will now be described in greater detail with reference to FIGS. 3, 4A, 4B, 5 and 6.

Figure 3:
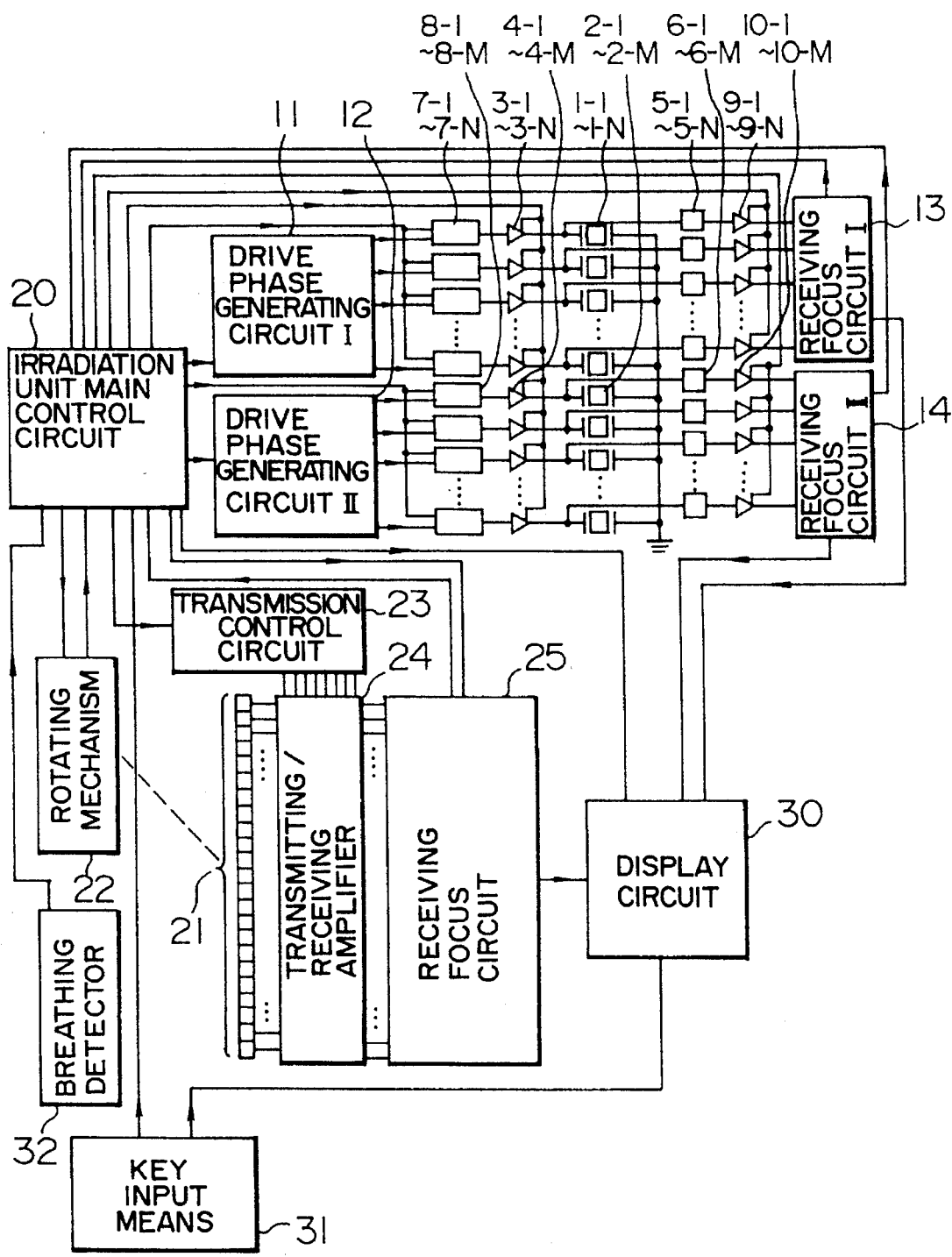
FIG. 3 is a block diagram showing the configuration of an embodiment of an ultrasonic irradiation apparatus according to the present invention.
Figure 4A:
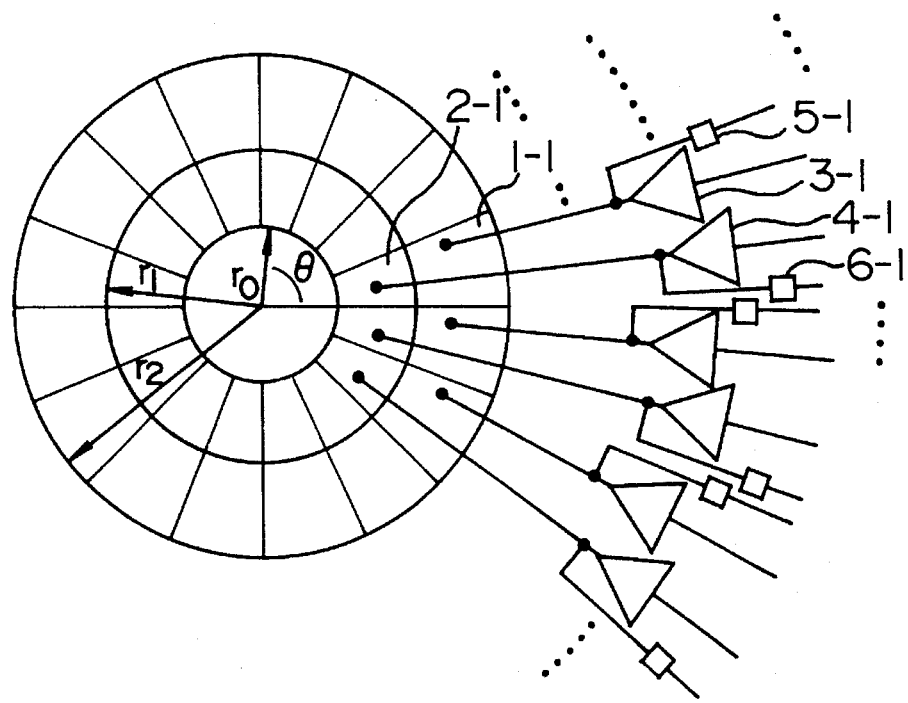
FIG. 4A is a top view showing an example of the configuration of an ultrasonic transducer unit in the embodiment of FIG. 3.
Figure 4B:
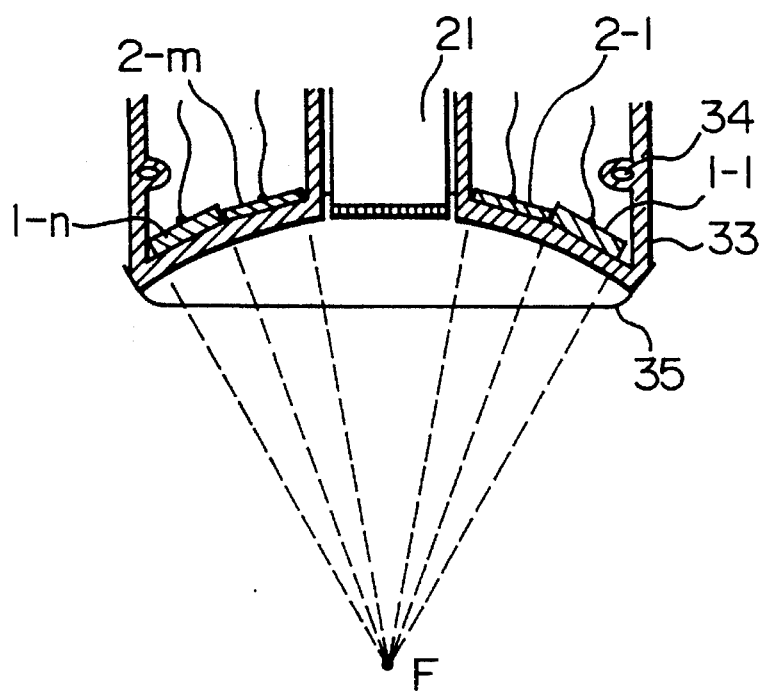
FIG. 4B is a side view showing the example of the configuration of the ultrasonic transducer unit in the embodiment of FIG. 3.
Figure 5:
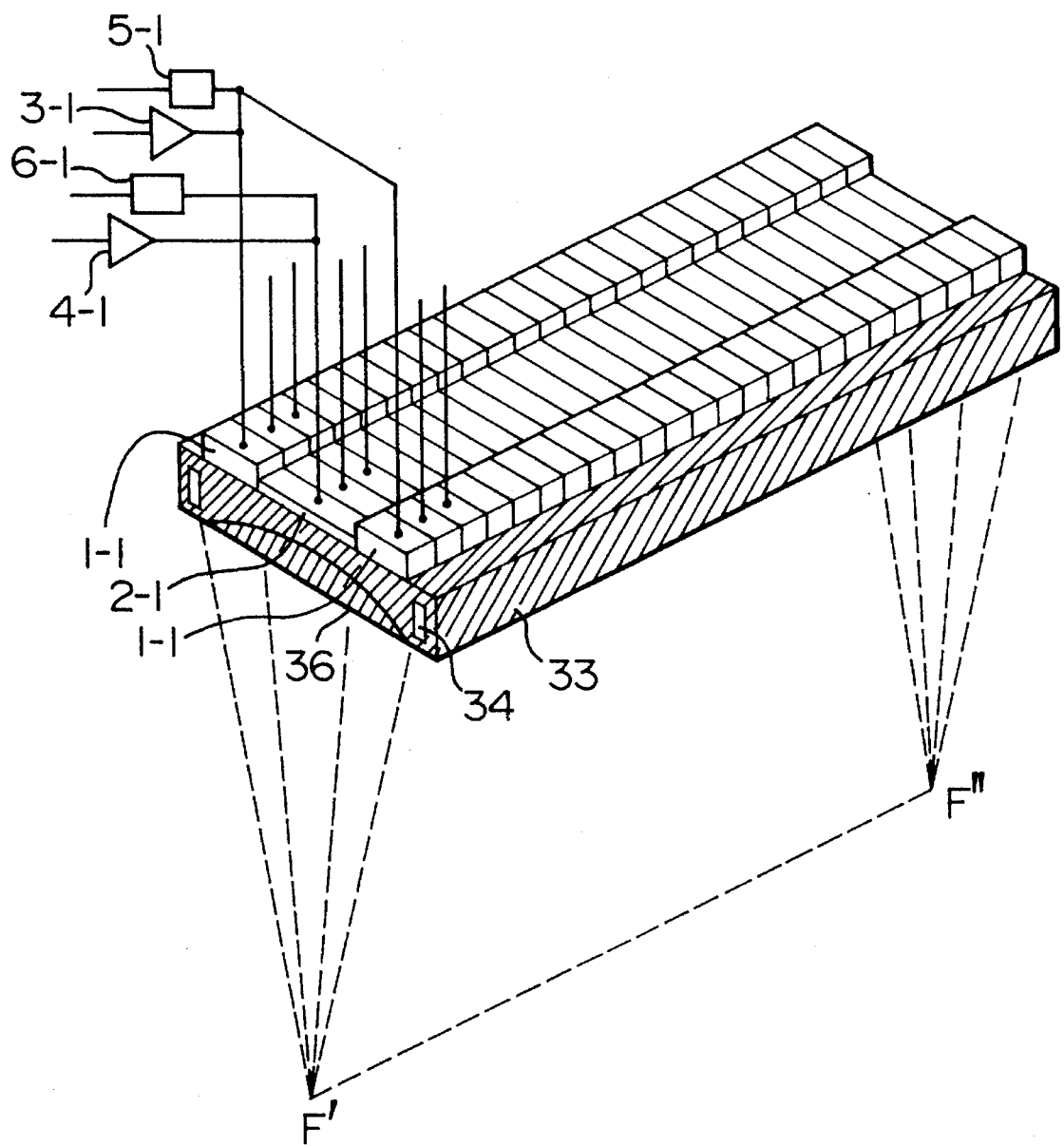
FIG. 5 is a diagram showing another example of the configuration of the ultrasonic transducer unit in the embodiment of FIG. 3.

The overall configuration of an embodiment of an ultrasonic irradiation apparatus according to the present invention having the function of monitoring the position where acoustic cavitation is generated is shown in FIG. 3 and the configuration of an ultrasonic transducer unit is shown in FIGS. 4A, 4B and FIG. 5.

Information concerning an ultrasonic irradiation therapeutic strategy is input from key input means 31 to an irradiation unit main control circuit 20 and on the basis of the information, irradiation focus/code signals for defining irradiation acoustic fields of a fundamental wave and a second harmonic wave as well as focus positions/acoustic pressure distribution forms of the respective waves are applied from the irradiation unit main control circuit 20 to a drive phase generating circuit I (11) and a drive phase generating circuit II (12), respectively. Drive phases of transducer elements for irradiating the generated fundamental wave and second harmonic wave are applied to drive signal generating circuits 7-1 to 7-N (N being the total number of independent transducer elements which are used for the fundamental wave) and drive signal generating circuits 8-1 to 8-M (M being the total number of ones of transducer independent elements which are used for the second harmonic wave), respectively. Drive amplitudes of the fundamental wave and the second harmonic wave are applied from the irradiation unit main control circuit 20 to the drive signal generating circuits 7-1 to 7-N and 8-1 to 8-M, respectively. Drive signals for the generated fundamental wave and the second harmonic wave are applied to element drive circuits 3-1 to 3-N and 4-1 to 4-M, respectively, to drive a group of irradiation transducer elements for the fundamental wave 1—1 to 1-N and a group of irradiation transducer elements for the second harmonic wave 2-1 to 2-M, respectively. The drive amplitudes can also be controlled by signals supplied from the irradiation unit main control circuit 20 directly to the element drive circuits 3-1 to 3-N and 4-1 to 4-M, thereby ensuring steady and easy operation of emergency stop of an ultrasonic irradiation upon the occurrence of abnormality.

An irradiation transducer composed an the group of fundamental wave elements 1—1 to 1-N and the group of second harmonic wave elements 2-1 to 2-M acts also as a receiving transducer for detection of cavitation generated in an irradiated object. Signals received by the respective elements are filtered to remove components of the irradiation signal band by means of band-reject filters 5-1 to 5-N and 6-1 to 6-M, then led to receiving amplifiers 9-1 to 9-N and 10-1 to 10-M, respectively, so as to be amplified thereby, and applied to a receiving focus circuit I (13) and a receiving focus circuit II (14), respectively. Since an output port of each of the fundamental wave drive circuits 3-1 to 3-N and an output port of each of the second harmonic wave drive circuits 4-1 to 4-M contains a series inductance which resonates with the sum of an element capacitance and a cable capacitance at the fundamental frequency $f_o$ or the second harmonic $2f_o$, the output impedance of the drive circuit will not act as a shunt at frequencies detuned from the respective $f_o$ or $2f_o$ to degrade the receiving sensitivity.

The receiving amplifiers 9-1 to 9-N and 10-1 to 10-M have variable gains and their gains are controlled by signals directly supplied from the irradiation unit main control circuit 20. During a time zone in which many unwanted signal components are generated off the irradiation ultrasonic center frequency, for example, during switching the irradiation focus, the gains are reduced to avoid saturation of the amplifiers. The respective receiving focus circuit I (13) and receiving focus circuit II (14) have parallel focus circuits for effecting focusing on a plurality of focal points arranged in an irradiation focusing region at a spacing corresponding to a spatial resolution of the receiving system, whereby they detect the generation and the generated positions of ultrasound components radiated by cavitation: subharmonic components having frequencies $f_o/2$ and $f_o/3$, harmonic components having frequencies $4f_o$, $6f_o$ and $8f_o$ and harmonic components of subharmonic components having frequencies $3f_o/2$, $5f_o/2$ and $7f_o/2$, etc. Signals indicative of cavitation generation positions and generation intensity are applied to a display circuit 30. Here, if parallel processing focus circuits which are smaller in number than the aforementioned focal points are used to scan the individual focal points, reduction of costs of the receiving focus circuit I (13) and receiving focus circuit II (14) can also be accomplished.

In the FIG. 3, 21 designates an array type transmitter/receiver probe dedicated to ultrasonic imaging and 22 designates a rotating mechanism for rotating the probe around an axis vertical to the probe surface, thus providing a configuration in which a plurality of ultrasonic pulse echo tomographic images necessary for positioning an irradiated object can be obtained. Respective elements of the probe 22 are connected to a transmission control circuit 23 and a receiving focus circuit 25 through a transmitting/receiving amplifier 24. The display circuit 30 is configured so that signals indicative of cavitation generation positions and generation intensity which are detected by the receiving focus circuit I (13) and receiving focus circuit II (14) are displayed while being superimposed on an obtained echo tomographic image.

In order to obtain good image resolution, the ultrasonic frequency band of the probe 21 is set to be $4f_o$ or higher. Structurally, harmonic components of, for example, frequencies $4f_o$, $6f_o$ and $8f_o$ and harmonic components of subharmonic components of, for example, $9f_o/2$ which are radiated by cavitation may be detected by the probe 21 rather than the group of elements 1—1 to 1-N and group of elements 2-1 to 2-M. Further, when the drive phase generating circuit I (11), drive phase generating circuit II (12) and drive signal generating circuits 7-1 to 7-N and 8-1 to 8-M are controlled by the irradiation unit main control circuit 20, pulse ultrasonic waves can be transmitted in synchronism with the transmission of imaging ultrasonic pulses by the array type transmitter/receiver probe 21 dedicated to ultrasonic imaging and focus positions of high-intensity ultrasonic waves for cavitation generation obtained through transmission by means of the elements 1—1 to 1-N and 2-1 to 2-M and reception by means of the probe 21 can be displayed while being superimposed on an echo tomographic image obtained through transmission and reception by means of the probe 21.

Since the efficiency of cavitation generation depends on the relative phase relation between the fundamental wave and the second harmonic wave, more highly efficient cavitation generation can be realized by controlling the drive signal generating circuits 7-1 to 7-N and 8-1 to 8-M such that the intensity of harmonic components and harmonic components of sub-harmonic components which are radiated by cavitation is maximized such that the relative phase relation is optimized. When the optimization according to the intensity of the harmonic components or the harmonic components of subharmonic components is difficult to achieve or when this function is desired to be omitted, there is also available a method for realizing highly efficient cavitation generation during at least more than a certain fraction of time by performing irradiation while shifting the relative phase relation by $\pi/8$ to $\pi/4$ with respect to the second harmonic wave. Not only when the optimum relative phase relation is searched for but also when the relative phase relation is shifted in accordance with a predetermined value, it is necessary to cause irradiation to continue for a constant time required for cavitation generation (typically, about 0.1 msec) or longer in one relative phase relation.

When observation of an ultrasonic irradiated object portion based on an echo tomographic image reveals that motion due to breathing of the object portion cannot be neglected and does matter, the irradiation focus is so controlled as to move in compliance with the motion of the object portion on the basis of a signal applied from the receiving focus circuit 25 to the irradiation unit main control circuit 20. When the motion of the object portion is so large that it exceeds the permissible range of irradiation focus or when tracking is difficult to achieve, the ultrasonic irradiation timing is controlled such that it is synchronized with breathing and ultrasonic irradiation is carried out within only a predetermined range of breathing timing, on the basis of a signal applied from a breathing detector 32 to the irradiation unit main control circuit 20.

Also, the efficient acoustic cavitation generating method of the present invention can be applied to improve imaging power possessed by the present embodiment implemented as an ultrasonic diagnostic apparatus. More particularly, by carrying out two-frequency superimposed ultrasound irradiation at relatively small intensity by using the group of elements 1—1 to 1-N and the group of elements 2-1 to 2-M and generating acoustic cavitation efficiently in an object imaged based on an ultrasonic pulse echo method using the probe 21 to emphasize an echo characteristic of the imaged object such as blood flow, a blood flow in a minute blood vessel or a low-speed blood flow can be imaged which can hardly be imaged even through the Doppler method when the ultrasonic pulse echo method using the probe 21 is employed alone.

Next, the ultrasonic transducer unit of the present embodiment will be described in greater detail with reference to FIGS. 4A, 4B and 5. As an example, FIGS. 4A and 4B show an array-type high-intensity ultrasonic transducer of 16 sectors×2 tracks composed of groups of ultrasonic elements 1—1 to 1-N and 2-1 to 2-M. FIG. 4A is a diagram showing the state of the transducer as seen from below with each group of elements associated with a part of peripheral circuits, and FIG. 4B is a diagram showing a sectional structure of the transducer.

This focusing type high-intensity ultrasonic transducer has a geometrical focus so that it may be allowed to scan focal points by means of a necessarily minimum number of elements N+M. In the present embodiment, the geometrical focus can be provided by disposing groups of ultrasonic elements 1—1 to 1-N and 2-1 to 2-M on a spherical shell 33 made of light metal. The spherical shell 33 made of light metal, containing as a main constituent magnesium or aluminum, has an ultrasonic irradiating surface side which is a concave surface forming part of a sphere having its center at a geometrical focal point F and has a back side which has a polyhedral form polished to allow ultrasonic elements of piezoelectric ceramic to be bonded thereto. Thanks to high thermal conductivity, the spherical shell 33 of light metal is effective to cool piezoelectric elements during high-intensity ultrasonic irradiation and also acts as an ground electrode of each piezoelectric element. The shell also forms part of a transducer housing and it is provided with a conduit 34 for cooling fluid for removing heat generated during high-intensity ultrasonic irradiation and mounted with a water bag 35 containing degassed water which enables easy acoustic coupling to the surface of the body. Since the light alloy, containing as a main constituent magnesium or aluminum, has an acoustic impedance which is intermediate between those of the piezoelectric ceramic and degassed water for coupling, the shell 33 serves also as an acoustic matching material between the two.

In the present embodiment, the thickness of the spherical shell 33 is as selected as to be a half wavelength of the fundamental wave or one wavelength of the second harmonic wave but the thickness may be changed for the part on which the fundamental wave elements 1—1 to 1-N on which the part of the second harmonic wave elements 2-1 to 2-M are mounted to be a ¼ wavelength of each of the frequencies, thereby improving transmitting/receiving characteristics of the pulse-like ultrasound.

Accommodated in a circular hole formed in a central portion of the array shown in FIGS. 4A and 4B is the pulse echo transmitter/receiver probe 21 dedicated to ultrasonic imaging. The basic structure of the probe 21 is identical to that of a sector scanning type array probe used in an ultrasonic diagnostic apparatus and in the present embodiment, its central frequency is set to be twice the resonance frequency of the second harmonic wave elements 2-1 to 2-M. In order to enable a single one-dimensional array probe to image a plurality of tomogram planes, the probe 21 is rotatable relative to the transducer housing 33 and is rotated about the central axis of the transducer by means of the rotating mechanism 22.

In the present embodiment, the transducer has a geometrical focal length of about 12 cm, an array outer diameter of about 12 cm, an inner diameter of about 4 cm and a diameter of about 8 cm of a circle for dividing the two tracks. Since the outer track for generating the fundamental wave has a diameter which is about twice the diameter of the inner track for generating the second harmonic wave, the diameter of a fundamental wave spot substantially equals that of a second harmonic wave spot on the focal plane and the generation of cavitation based on the synergistic effect of the two frequencies can be carried out effectively.

When for the 12 cm array outer size the inner diameter is set to 3 cm and the diameter of the circle dividing the two tracks is set to 6 cm, the outer track and the inner track are almost exactly analogous to each other in terms of the ratio between wavelengths and therefore a peak acoustic pressure distribution of the second harmonic wave approximately equals that of the fundamental wave on the focal plane.

With the present configuration, the fundamental wave and the second harmonic wave are irradiated simultaneously on only the vicinity of the focal point and therefore by setting the focal point in an irradiated object, cavitation can efficiently be generated locally only in the vicinity of the focal point.

FIG. 5 shows an example in which a rectangular array is used as the ultrasonic transducer unit in the present embodiment. In FIG. 5, parts having the same function and the same name as parts in FIGS. 4A and 4B are designated by identical numerals. An ultrasonic transducer formed of a rectangular piezoelectric ceramic having a minor side of 4 cm and a major side of 16 cm is divided into 2N+M elements and 2N elements on opposite ends of the minor side are electrically connected together to form an array transducer consisting of N electrically independent fundamental wave generating elements 1-1 to 1-N and M electrically independent second harmonic wave generating elements 2-1 to 2-M. An irradiation surface side of an acoustic matching layer 33 made of a light alloy, containing as a main constituent magnesium or aluminum, forms part of a cylindrical surface and its concave portion is filled with an acoustic filler 36 made of a polymer material which exhibits a acoustic speed comparable to or slower than that of water and which has its surface formed to be flat or convex, so that the transducer as a whole forms geometrical foci on a line segment F'F".

The ultrasonic transducer according to the embodiment of FIG. 5 has a basic structure which functions also as a linear scanning type or sector scanning type array probe used in the ultrasonic diagnostic apparatus. Accordingly, by using a part of the basic structure shown in FIG. 3 obtained by eliminating the probe 21 dedicated to ultrasonic imaging and its rotating mechanism 22, the transmission control circuit 23, the transmitting/receiving amplifier 24 and the receiving focus circuit 25, an ultrasonic pulse echo tomographic image necessary for positioning an irradiated object can be obtained. But, like the ordinary linear scanning type or sector scanning type probe, this transducer can image only a tomogram plane which extends in a direction parallel to the major side. Since the fundamental wave generating elements electrically connected in common have a width in the minor side direction which is set to be about twice a width in the minor side direction (a direction orthogonal to the array arrangement direction) of the second harmonic wave generating elements, a fundamental wave spot and a second harmonic wave spot expand substantially equally in the minor side direction on the focal plane and the generation of cavitation due to the synergistic effect of the two frequencies can be carried out efficiently. In the case of the present configuration, too, the fundamental wave and the second harmonic wave are synthesized in a medium and the two-frequency waves are irradiated simultaneously on only the vicinity of the focal point and therefore, by setting a focal point in an irradiated object, cavitation can efficiently be generated locally only in the vicinity of the focal point. In an application of sono-chemical reactions induced by the cavitation for therapeutic purposes, this leads to an advantage that the possibility of producing side effects at a portion in front of or behind an irradiated object can be substantially eliminated.

Figure 6:
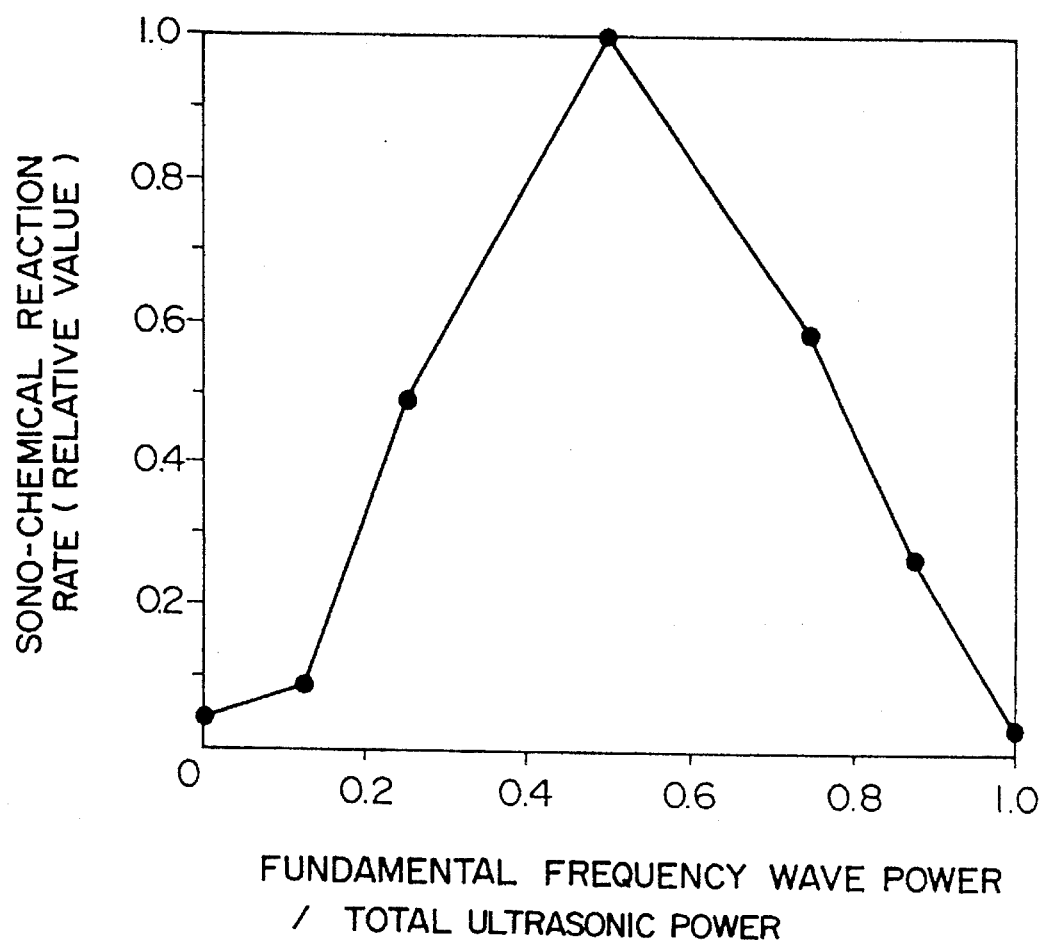
FIG. 6 is a diagram showing experimental results of a sono-chemical reaction due to the second superimposed wave.

Referring to FIG. 6, an example will be described wherein by irradiating ultrasonic waves by means of the ultrasonic irradiation apparatus including the ultrasonic transducer of FIGS. 4A and 4B and having the overall configuration of FIG. 3, sono-chemical effects are practically generated with efficiency in an aqueous solution. An experiment was conducted for a sono-chemical reaction in which molecular iodine was released from iodide ions by oxidation. An aqueous solution of potassium iodide with chloral hydrate added was poured in a test tube made of polystyrene (which has a higher transparency for ultrasound than glass), placed at the focal point of the focusing type ultrasonic transducer and irradiated with ultrasound. The concentration of released iodine was determined by absorbance and the rate of the sono-chemical reaction was determined from the absorbance.

In FIG. 6, the sono-chemical reaction rate obtained when a fundamental wave of 750 kHz and a second harmonic wave of 1.5 MHz are irradiated simultaneously with the sum of power levels of the two waves being kept constant is plotted in relation to the ratio of fundamental wave power to total ultrasonic power. In that case, the sum of the fundamental frequency ultrasonic wave intensity and second harmonic ultrasonic wave intensity was about 30 W/cm$^2$ in the vicinity of the focal point. While the sono-chemical reaction rate for the fundamental wave or second harmonic wave alone was zero within the experimental error range, the synergistic effect obtained by the simultaneous irradiation of the two waves was remarkable, and especially, a high sono-chemical reaction rate was obtained at a ratio of the fundamental wave power to the total ultrasonic power which was from 0.2 to 0.8 (fundamental wave:second harmonic wave=1:4 to 4:1).

Referring now to 13, 14A, 14B, and 15 to FIGS. 7 to 20, an embodiment will be described in greater detail wherein wave transmitter elements used for transmission/reception of the fundamental wave are identical to those used for transmission/reception of the second harmonic wave.

To describe a transmitter element, it is formed of a piezoelectric material and a material having an acoustic impedance equal to that of the piezoelectric material and its total thickness is set to correspond to a half wavelength of the fundamental wave so that not the total thickness but a partial thickness region of the transmitter element may be driven piezoelectrically, thereby making the transmitter element active at both the fundamental frequency and the second harmonic which is twice the fundamental frequency. This expedient is for avoiding an inconvenience that the wave transmitter element becomes piezoelectrically inactive at frequencies of even multiples of the fundamental resonance frequency if the thickness as a whole is driven piezoelectrically as in the ordinary piezoelectric element.

Also, a drive circuit operated as usual with a drive waveform in the form of a sine wave or a rectangular wave having good symmetry is unsuitable for generating ultrasonic waves of frequencies of even multiples from the piezoelectric vibrator element because the drive waveform does not contain frequencies of even multiples of the fundamental frequency and therefore it is necessary to contrive a drive circuit which is operated with a drive waveform in the form of a waveform containing intended frequency components. A first expedient is that when a rectangular wave is used as the drive waveform, the ratio of the durations of the high and low levels of the rectangular wave is not set to be 1:1 as in the usual case but is set to be asymmetrical. A second expedient concerning the drive circuit is that in place of a rectangular wave, a sawtooth wave or a stepped wave simulating the sawtooth wave is used as the drive waveform. A third expedient concerning the drive circuit is that a capacitor and an inductance are added to the piezoelectric vibrator element to form a resonance circuit which resonates at both the fundamental frequency and the second harmonic and this resonance circuit is driven by a circuit driven at the fundamental frequency and by a circuit driven at the second harmonic.

Figure 8:
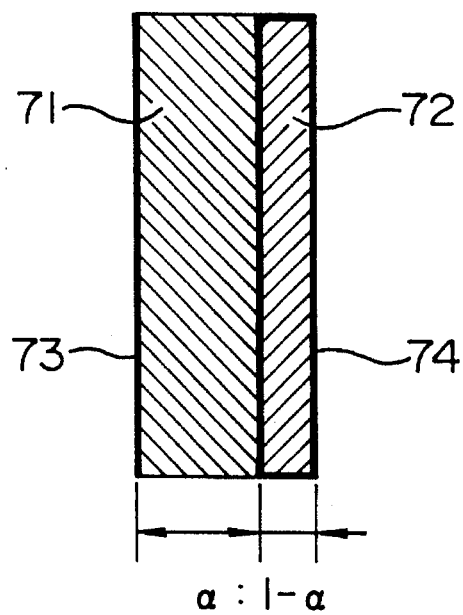
FIG. 8 is a sectional view showing the configuration of a piezoelectric thickness mode vibrator element of an ultrasonic transducer unit in the embodiment of FIG. 7.

In connection with a piezoelectric thickness made vibrator element formed of a piezoelectric material and a material having an acoustic impedance equal to that of the piezoelectric material and having a thickness of a half wavelength of the fundamental wave, a structure as shown in FIG. 8 is considered wherein a region corresponding to an acoustic thickness (a thickness corrected for non-uniformity when the vibrator element is not uniform for the sound speed of the resonance mode in question) of $\alpha$ measured from an end is driven piezoelectrically. Of the piezoelectric structure, a portion 71 driven piezoelectrically and a portion 72 not driven piezoelectrically are united acoustically by sintering or by means of a high-intensity bonding agent. In the example of FIG. 8, an electric field is applied across an electrode 74 covering the portion 72 and an electrode 73. The portion 72 covered with the electrode 74 represents the portion which is not driven piezoelectrically.

Electromechanical conversion efficiencies $\epsilon_0$ and $\epsilon_1$ exhibited by this piezoelectric vibrator element at the fundamental frequency and the second harmonic are expressed by $$\epsilon_0 = E\sin^4(\pi\alpha/2) \quad (1)$$

$$\epsilon_1 = E\sin^4 \pi\alpha \quad (2)$$

where E is a constant determined by the material and the like. The usual structure in which the whole thickness is driven piezoelectrically corresponds to the case of $\alpha=1$ and in this case, from (Equation 1) and (Equation 2), $\epsilon_0=E$ and $\epsilon_1=0$, indicating that while the fundamental wave can be converted, the second harmonic wave cannot be converted. The reason is because under the resonance state at the second harmonic, when a half of the thickness is distorted in the compression direction, the remaining half is required to be distorted in the expansion direction but this structure is allowed to be driven in only the mode in which the whole thickness is distorted uniformly in the compression direction or the expansion direction. Contrarily, for $\alpha=2/3$, $\epsilon_0=\epsilon_1=9/16 E$ is obtained from (Equation 1) and (Equation 2), indicating that the fundamental wave and the second harmonic wave can both be converted with the same conversion efficiency.

The drive waveform will now be described by referring first to the case of a rectangular wave. Power $\zeta_0$ and power $\zeta_1$ of the fundamental frequency component and second harmonic component contained in a rectangular wave in which the ratio of the durations of the high and low levels of the rectangular wave is $\beta:(1-\beta)$ are expressed by $$\zeta_0 = F\sin^2 \pi\beta \quad (3)$$

$$\zeta_1 = (F/4)\sin^2 \pi\beta \quad (4)$$

where F is a constant determined by a difference between the high and low levels, that is, the amplitude or the like. The usual rectangular wave having good symmetry corresponds to the case of $\beta=\frac{1}{2}$ but in this case, from (Equation 3) and (Equation 4), $\zeta_0=F$ and $\zeta_1=0$, indicating that the fundamental frequency component is contained in the rectangular wave but the second harmonic component is not contained in the rectangular wave. Contrarily, for $\beta=\frac{1}{4}$, from (Equation 3) and (Equation 4), $\zeta_0=F/2$ and $\zeta_1=F/4$, indicating that a drive waveform containing both the fundamental frequency component and the second harmonic component can be obtained. At that time, the magnitude of $\zeta_1$ is maximized.

Figure 10:
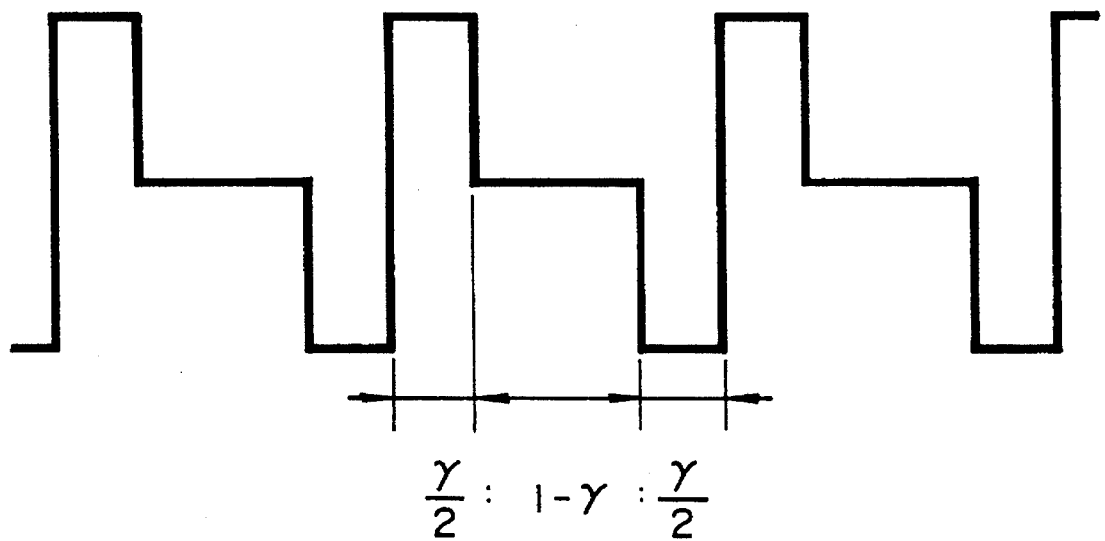
FIG. 10 is a diagram showing an example of a stepped drive waveform for the piezoelectric thickness mode vibrator element of FIG. 8.

Next, the case where a sawtooth wave or a stepped wave simulating the sawtooth wave is used as the drive waveform will be described. Since it is well known that the sawtooth wave has frequency components of even multiples of the fundamental frequency, the stepped wave simulating the sawtooth wave will be described herein in greater detail. Power $\eta_0$ and power $\eta_1$ of the fundamental frequency component and second harmonic component contained in a stepped wave as shown in FIG. 10 in which the of the total duration of the high and low levels of the stepped wave and the duration of the intermediate level of the stepped wave is $\gamma:(1-\gamma)$ are expressed by $$\eta_0 = G\sin^4(\pi\gamma/2) \quad (5)$$

$$\eta_1 = (G/4)\sin^4 \pi\gamma \quad (6)$$

where G is a constant determined by a difference between the high and low levels, that is, the amplitude and the like. The usual rectangular wave having good symmetry corresponds to the case of $\gamma=1$ but in this case, from (Equation 5) and (Equation 6), $\eta_0=G$ and $\eta_1=0$, indicating that the fundamental frequency component is contained in the stepped wave but the second harmonic component is not contained in the stepped wave. Contrarily, for $\gamma=\frac{1}{2}$, $\zeta_0=\zeta_1=F/4$ is obtained from (Equation 3) and (Equation 4), indicating that a drive waveform containing the fundamental frequency component and the second harmonic component equally can be obtained.

Figure 11:
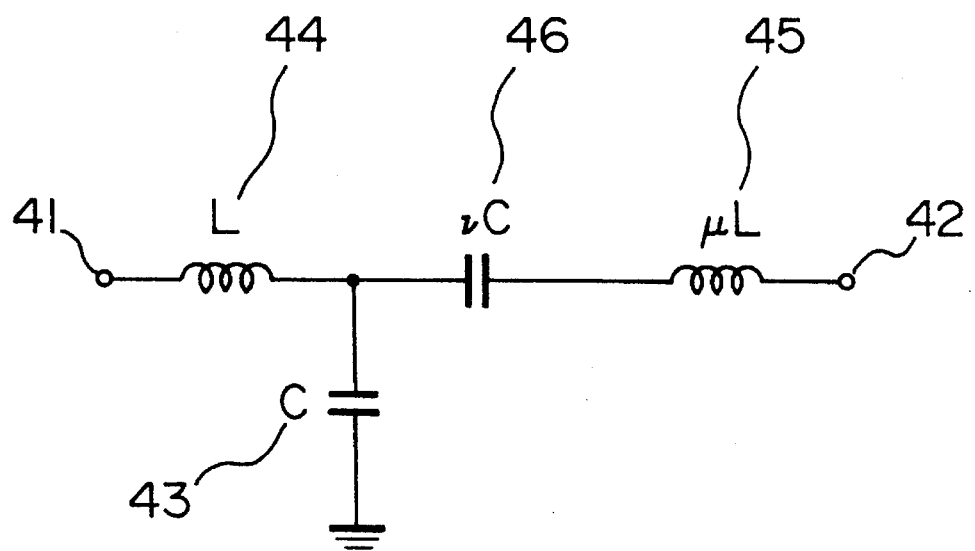
FIG. 11 is a diagram showing the configuration of the peripheral circuit of a piezoelectric vibrator element of the ultrasonic transducer unit in the embodiment of FIG. 7.

As shown in FIG. 11, when a circuit in which a capacitor is connected in parallel with a piezoelectric vibrator element to provide a total capacitance C (43) and inductances L (44) and $\mu L$ (45) and a capacitance $vC$ (46) are added, can be assumed to have terminals 41 and 42 connected to a drive circuit having a sufficiently low output impedance, electrical impedances Z1 and Z2 as viewed from the terminals 41 and 42 can be expressed by $$Z_1 = D/(1+v-\mu v\omega^2 CL) \quad (7)$$

$$Z_2 = D/v/(1-\omega^2 CL) \quad (8)$$

where $\omega$ represents angular velocity and $$D = [1-(1+v+\mu v)\omega^2 CL + \mu v\omega^4 C^2 L_2]/j\omega C \quad (9)$$

holds when j represents an imaginary unit. For $\mu=16/9$ and $v=9/25$, from the above equations, $$Z_1 = D'/(17/8-\omega^2 CL) \quad (10)$$

$$Z_2 = D'/[9/16(1-\omega^2 CL)] \quad (11)$$

$$D' = (5/8-\omega^2 CL)(5/2-\omega^2 CL) \quad (12)$$

are obtained. At that time, on the basis of (Equation 12), $Z_1$ and $Z_2$ are both minimized when $\omega^2 CL=5/8$ or $5/2$. In other words, a circuit can be obtained which is characteristic of resonating at two frequencies being at a ratio of 1:2. On the basis of (Equation 11), $Z_1$ and $Z_2$ are maximized at $\omega^2 CL=17/8$ and 1, respectively, and therefore it is advantageous to construct the circuit such that the terminals 41 and 42 are driven at the fundamental frequency and the second harmonic, respectively.

Figure 12:
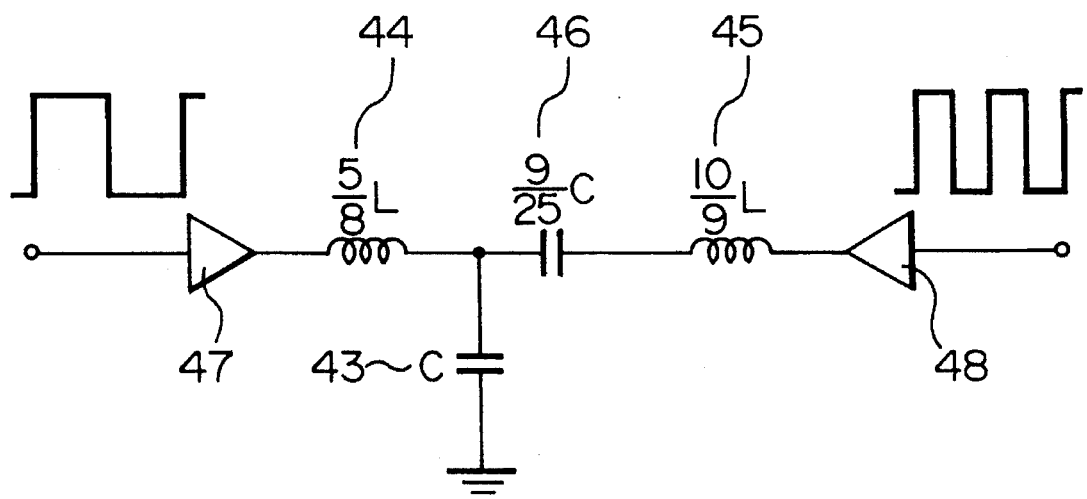
FIG. 12 is a diagram showing an example of the configuration of the circuit to drive a piezoelectric vibrator element of the ultrasonic transducer unit in the embodiment of FIG. 7.
Figure 13:
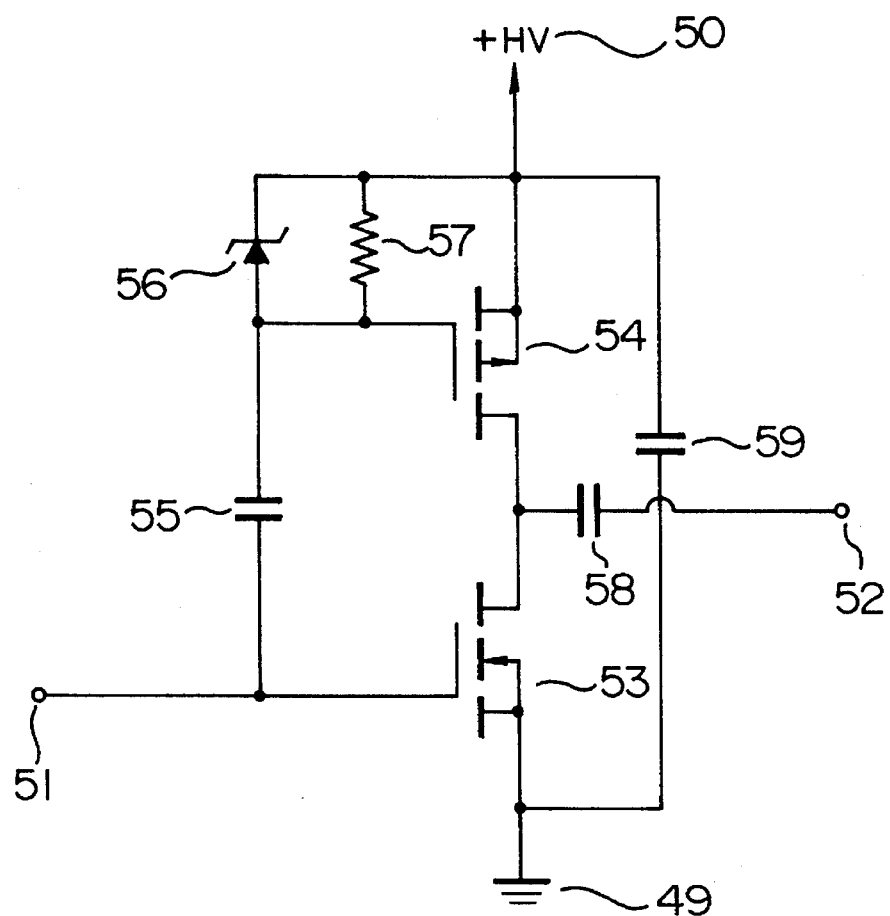
FIG. 13 is a diagram showing an example of a push-pull type switching circuit constituting the circuit to drive piezoelectric vibrator element of the ultrasonic transducer unit in the embodiment of FIG. 7.
Figure 14A:
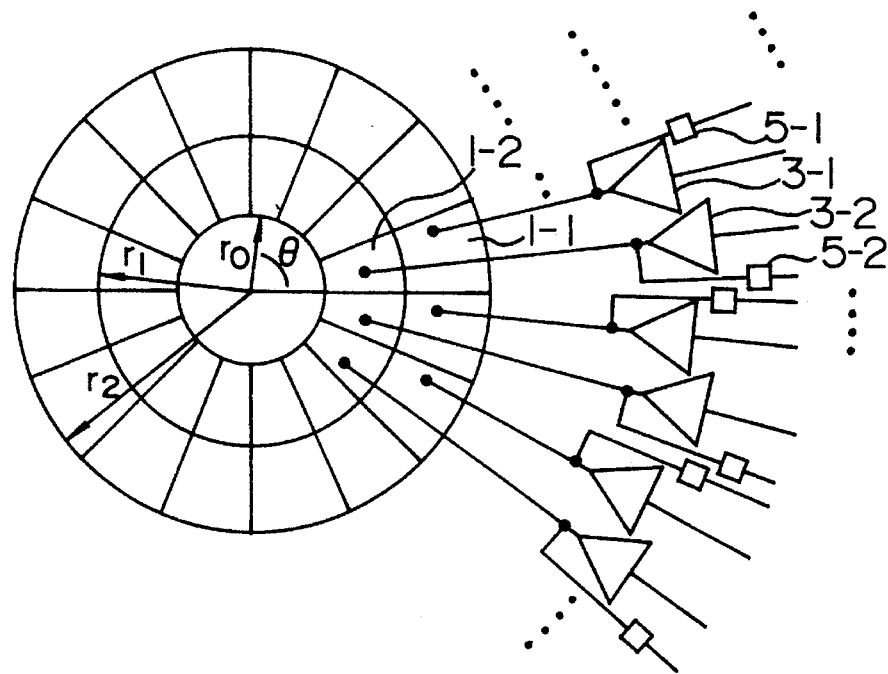
FIG. 14A is a top view showing the configuration of an example of the ultrasonic transducer unit in the embodiment of FIG. 7.
Figure 14B:
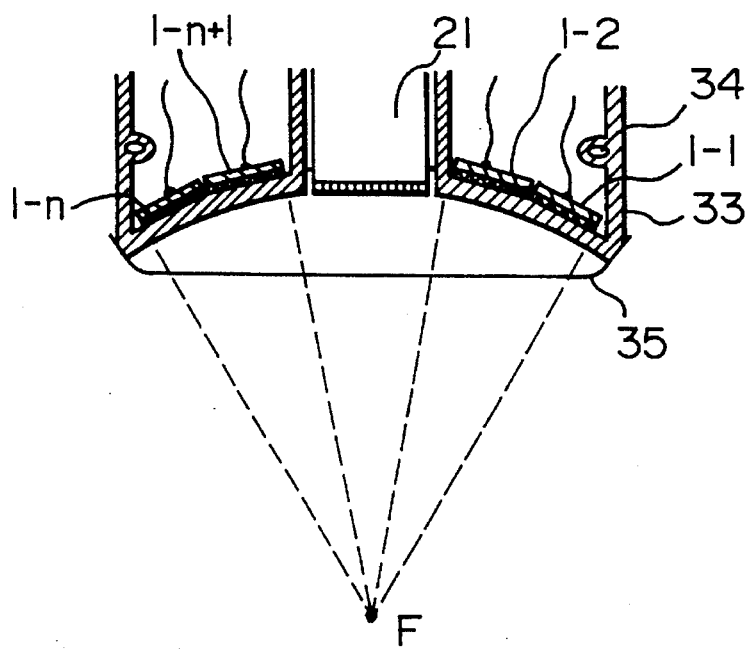
FIG. 14B is a side view showing the configuration of the example of the ultrasonic transducer unit in the embodiment of FIG. 7.

The overall configuration of an embodiment of an ultrasonic irradiation apparatus according to the present invention using the wave transmitter element contrived as above and having a function for monitoring the acoustic cavitation generating position is shown in FIG. 7, the configuration of an element drive circuit unit is shown in FIGS. 12 and 13, and the configuration of an ultrasonic transducer unit is shown in FIGS. 14A and 14B.

This embodiment is identical to the embodiment of FIG. 3 with the exception that the wave transmitting element is used in common to the fundamental wave and the second harmonic wave. Information concerning ultrasonic irradiation therapeutic strategy is input from key input means 31 to an irradiation unit main control circuit 20 and on the basis of the information, irradiation focus/code signals for defining focus positions/acoustic pressure distribution forms are applied from the irradiation unit main control circuit 20 to a drive phase generating circuit 11. Drives Phases of transducer elements for irradiating the generated fundamental wave and second harmonic wave are applied to drive signal generating circuits 7-1 to 7-N (N being the total number of independent transducer elements), respectively. Control signals for drive amplitudes of the fundamental wave and the second harmonic wave are supplied from the irradiation unit main control circuit 20 to the drive signal generating circuits 7-1 to 7-N. Generated drive signals are supplied to element drive circuits 3-1 to 3-N to drive a group of transducer elements 1—1 to 1-N for irradiation. The drive amplitudes can also be controlled by signals applied from the irradiation unit main control circuit 20 directly to the element drive circuits 3-1 to 3-N, thereby ensuring steady and easy operation of an emergency stop of ultrasonic irradiation upon the occurrence of an abnormality.

FIG. 12 shows the configuration of a circuit of one element of the element drive circuits 3-1 to 3-N and FIG. 13 shows the configuration of a push-pull type switching circuit forming a part of the circuit shown in FIG. 12. Output ports of a fundamental wave driver 47 and a second harmonic wave driver 48 are connected to each element through a circuit which has the basic configuration of FIG. 11 and which resonates at the fundamental frequency $f_o$ and the second harmonic $2f_o$. In FIG. 12, capacitance C and inductance L form a combination which resonates at the fundamental frequency $f_o$. In other words, $$(2\pi f_o)^2 CL = 1 \quad (13)$$

holds.

A switching circuit in FIG. 13 is configured such that the connections of a constant potential source 49 on the low potential side (in this case, earth potential) and a constant potential source 50 on the high potential side to an output terminal 52 are switched on and off by means of switching elements 53 and 54, respectively. The output terminal 52 is connected through a capacitor 58 so as to deliver only AC components. For stabilization of power supply potential, a capacitor 59 is connected between the constant potential sources 49 and 50. An input terminal 51 is connected directly to a gate of the switching element 53 on the ground potential side but is connected through a capacitor 55 to a gate of the switching element 54 on the high potential side. The DC level on the gate of the switching element 54 is controlled by the action of a Zener diode 56 having a Zener potential level of a gate drive signal amplitude (the difference between maximum potential and minimum potential) such that the maximum potential of the gate drive signal equals the potential of the constant potential source 50 on the high potential side. In order to prevent runaway of the DC level, a resistor 57 is connected in parallel with the Zener diode 56.

The irradiation transducer configured of the group of elements 1—1 to 1-N operates also as a receiving transducer for detection of cavitation generated in an irradiated object. Signals received by the individual elements are filtered to remove components of the irradiation signal band by means of band-reject filters 5-1 to 5-N and are then led to receiving amplifiers 9-1 to 9-N so as to be amplified thereby and applied to a receiving focus circuit 13. Since the output port of each of the element drive circuits 3-1 to 3-N is connected to the low impedance circuit through the resonance circuit operative to resonate at the frequencies $f_o$ and $2f_o$ as described above, the output impedance of the drive circuit will not act as a shunt at frequencies detuned from the respective $f_o$ and $2f_o$ to degrade the receiving sensitivity..

Display of an echo tomographic image by the array type transmitter/receiver probe 21 dedicated to ultrasonic imaging and motion due to breathing of the object portion can be dealt with in the same way as that in the embodiment of FIG. 3 and will not be described.

Referring now to FIGS. 14A and 14B, the difference between the ultrasonic transducer unit of the present embodiment and the ultrasonic transducer unit shown in FIGS. 4A and 4B will now be described. A diagram of FIG. 14A showing the state of the transducer as seen from below and the elements associated with a part of peripheral circuits is the same as FIG. 4A.

In a piezoelectric element shown in FIG. 14B, a plate-type piezoelectric ceramic having a thickness of ⅓ wavelength of the fundamental wave (=⅔ wavelength of the second harmonic wave) is strongly bonded by a bonding agent of relatively small thermal expansion coefficient with a plate which is made of the same piezoelectric ceramic material but is made to be essentially piezoelectrically inactive by short-circuiting electrodes or without applying the electrode polarizing processing and which has a thickness of ⅙ wavelength of the fundamental wave. This piezoelectrically inactive plate may also be made of a piezoelectrically inactive material such as zinc or copper having an acoustic impedance which is approximately equal to that of the piezoelectric ceramic. With this configuration, an ultrasonic vibrator element having piezoelectric activity at both the frequencies of the fundamental frequency and second harmonic is realized. FIG. 14B differs from FIG. 4B only in that the wave transmitter elements 1—1 and 1-2 are depicted as having the same thickness in FIG. 14B.

Even with a structure in which a spherical shell 33 forming part of the housing is not made of a light alloy but is made of zinc or copper and has a thickness of ⅙ wavelength of the fundamental wave and a piezoelectric ceramic element having a thickness of ⅓ wavelength of the fundamental wave bonded to the spherical shell 33, the piezoelectric activity can be obtained at the frequencies of both the fundamental frequency and the second harmonic but the structure of FIGS. 14A and 14B is slightly superior from the view of acoustic separation between adjacent elements.

Acommodated in a circular hole at an array central portion shown in FIGS. 14A and 14B is a pulse echo transmitter/receiver probe 21 dedicated to ultrasonic imaging as in the case of FIGS. 4A and 4B.

Figure 15:
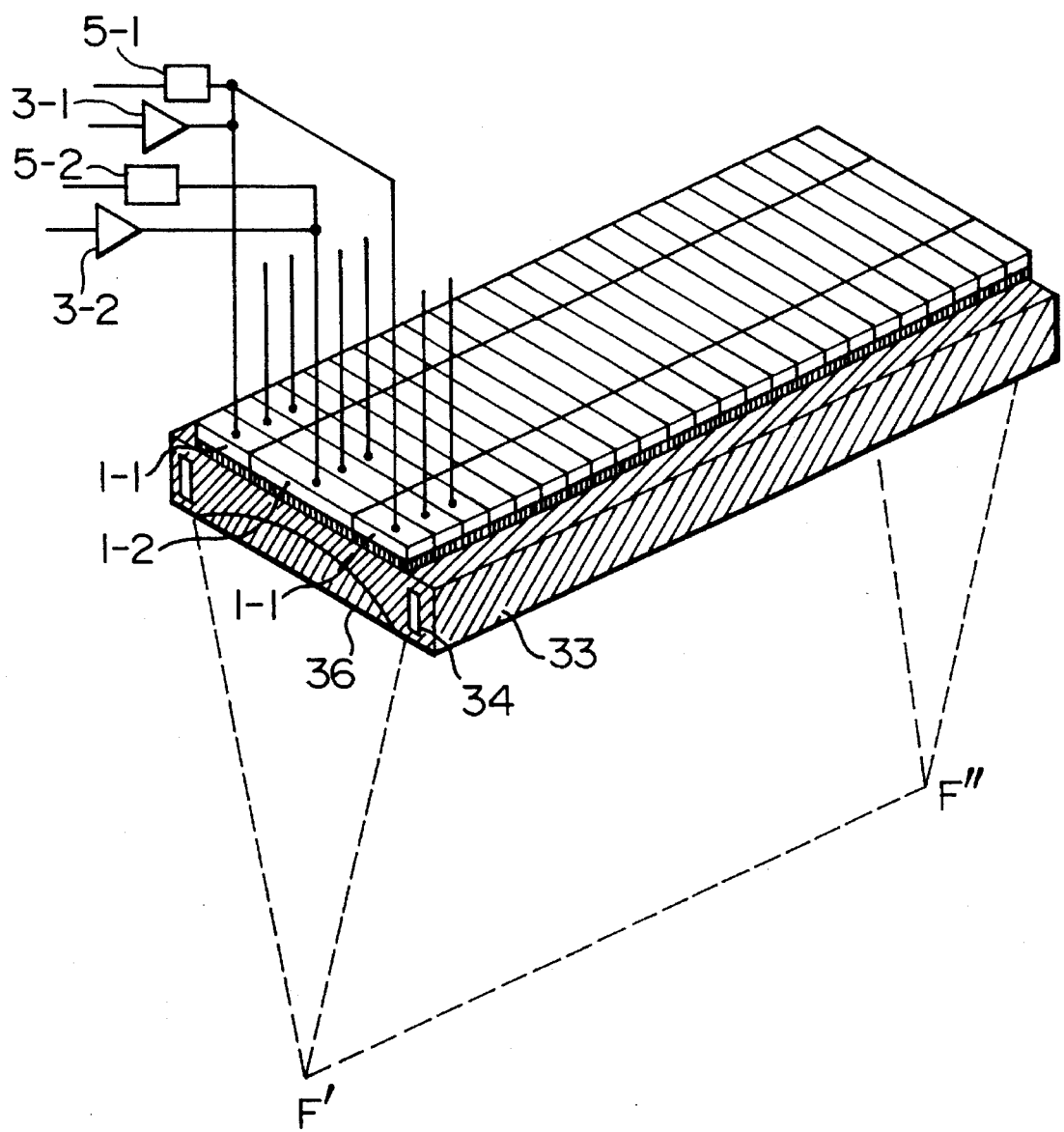
FIG. 15 is a diagram showing another example of the configuration of the ultrasonic transducer unit in the embodiment of FIG. 7.

FIG. 15 shows an example in which a rectangular array is used as the ultrasonic transducer unit of the present embodiment. Like the relation of FIGS. 14A and 14B to FIGS. 4A and 4B, FIG. 15 differs from FIG. 5 in that wave transmitter elements 1—1 and 1-2 are depicted as having the same thickness. The two group of elements 1—1, 1-3, . . . on opposite sides of the group of elements 1-2, 1-4, . . . are mutually connected to the corresponding element drive circuits 3-1, 3—3, . . . , but can be driven at different phases relative to the group of elements 1-2, 1-4, making it possible to move the focal point in the depth direction along the minor side.

Figure 9:
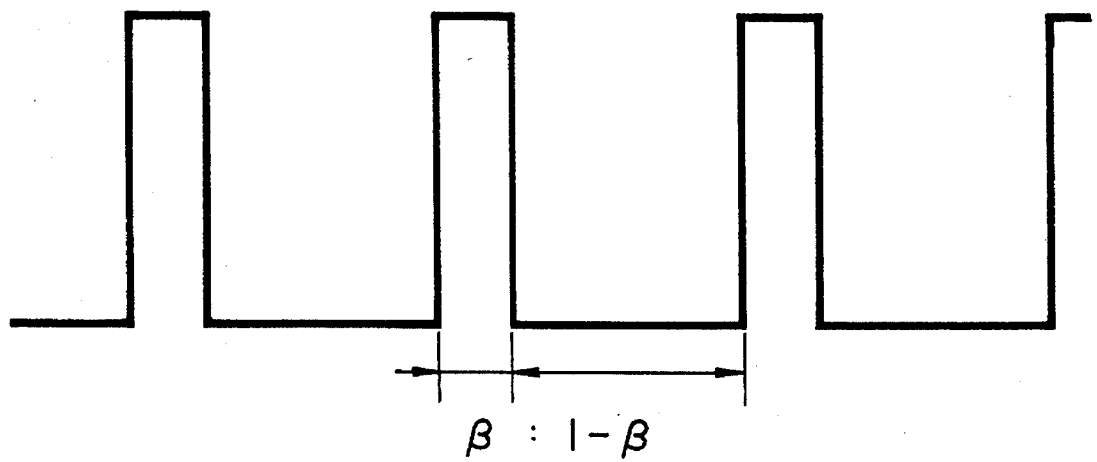
FIG. 9 is a diagram showing an example of a rectangular drive waveform for the piezoelectric thickness mode vibrator element of FIG. 8.

In the foregoing, the circuit configuration capable of superimposing the second harmonic wave on the fundamental wave in a desired phase relation thereto at a desired amplitude ratio and the apparatus configuration including the same have been described, but if it suffices that this limitation is relieved to allow only a second harmonic wave being in a constant phase relation to the fundamental wave to be superimposed thereon, the superimposition of the second harmonic wave can be effected with a simpler circuit configuration. When a waveform as shown in FIG. 9 is desired to be obtained as a result of the superimposition, that is, when the second harmonic wave is superimposed on the fundamental wave in a cosine-wave to cosine-wave relation, the push-pull type circuit as shown in FIG. 13 may be used with one circuit per element. Namely, when the two switching elements 53 and 54 constituting the push-pull type circuit are controlled such that a state of turning 53 on and rendering 54 off and a state of turning 53 off and turning 54 on are repeated, an ultrasound at the fundamental frequency and an ultrasound at the second harmonic frequency can be irradiated at the same time by controlling the ratio of durations of the high and low levels of the waveform shown in FIG. 9 to a ratio which is not 1:1 but is of an unequal ratio such as 1:3.

Figure 16:
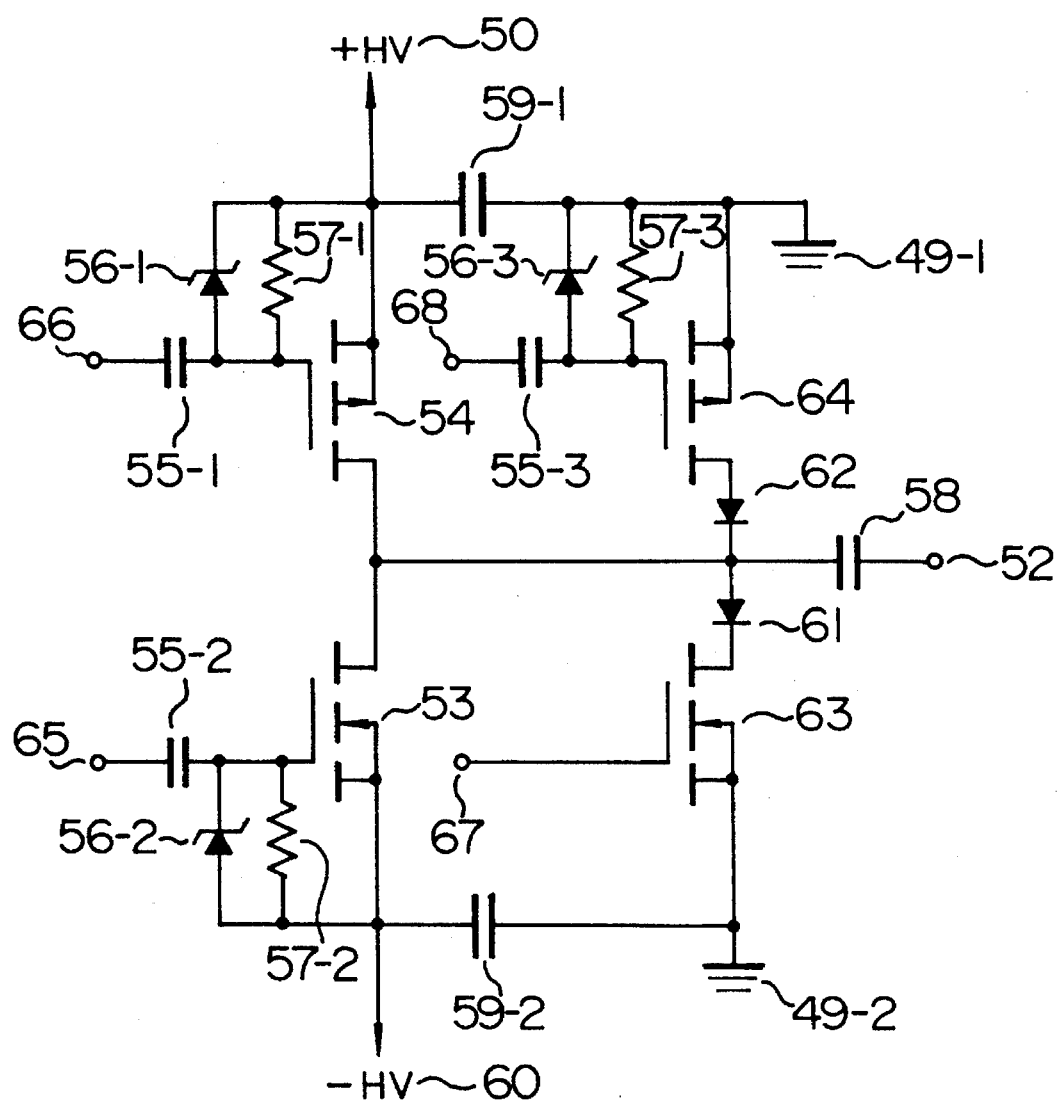
FIG. 16 is a diagram showing another example of the circuit to drive a piezoelectric vibrator element of the ultrasonic transducer in the embodiment of FIG. 7.
Figure 17:
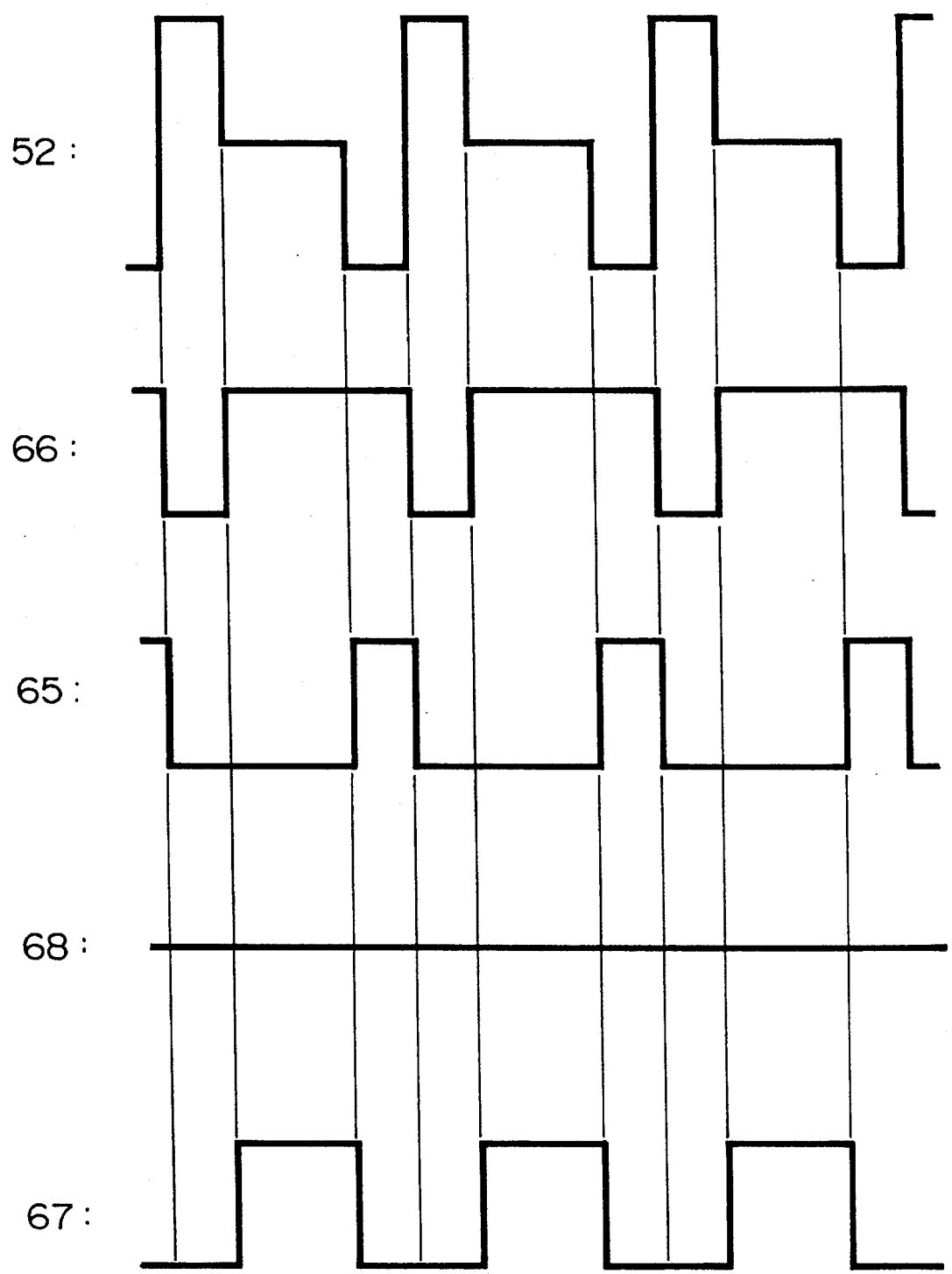
FIG. 17 is a time chart for generating a drive stepped waveform for the piezoelectric thickness mode element of FIG. 8 with the circuit shown in FIG. 16.

When a waveform as shown in FIG. 10 is desired to be obtained as a result of the superimposition, that is, when the second harmonic wave is desired to be superimposed on the fundamental wave in a sine-wave to sine-wave phase relation, a circuit configuration as shown in FIG. 16 is needed. One circuit of this type is used per element to drive the piezoelectric vibrator element. By controlling gate input terminals 66, 65, 68 and 67 of drive circuits composed of switching element groups 54, 53, and the confirmation of 64 and 63, i.e. three groups per piezoelectric vibrator element, adapted to switch on and off the electrical connection between three respective constant potential sources 50, 60 and the combination of 49-1 and 49-2 and the piezoelectric vibrator element in accordance with time chart shown in FIG. 17, a drive waveform having a steeper rise than fall as shown in FIG. 10 can be obtained as an output waveform at output terminal 52. By changing the time chart, a drive waveform can also be obtained which is steeper when falling than when rising. In contrast with the case for obtaining the drive waveform of FIG. 17 in which the gate input terminal 68 remains off, the gate control of terminal 68 similar to that applied to the gate input terminal 68 in the case of FIG. 17 is carried out. According to the circuit configuration of FIG.

16, since the drive waveform which can be obtained with the FIG. 13 circuit configuration can of course be obtained, driving can be achieved based on a second harmonic superimposed wave which is desirably defined at least with respect to a phase relation. The input terminal 67 is connected directly to a gate of the switching element 63 but the other input terminals 65, 66 and 68 are connected to gates of the switching elements 53, 54 and 64, respectively, through circuits similar to the gate peripheral circuit of the switching element 54 in FIG. 13. In order to prevent reverse currents through the switching elements 63 and 64, these elements are connected in series with diodes 61 and 62.

Figure 18:
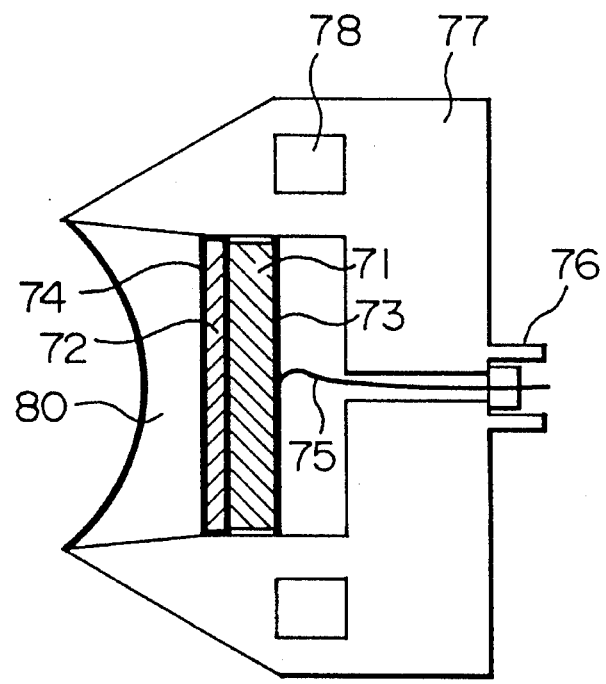
FIG. 18 is a sectional view of an example of a single focus manual or mechanical scanning type transducer usable in the present invention.
Figure 19:
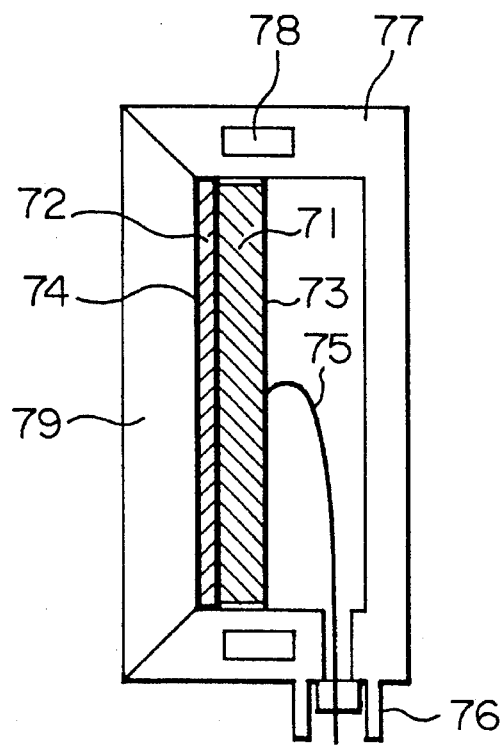
FIG. 19 is a sectional view of an example of a non-focus type plane wave transducer usable in the present invention.
Figure 20:
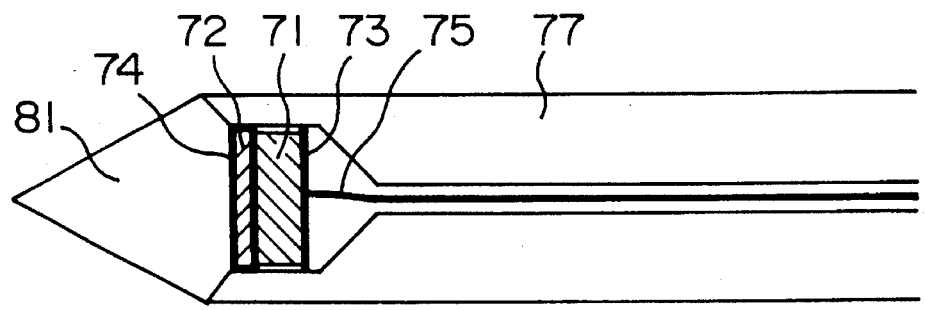
FIG. 20 is a sectional view of an example of a stylus or needle-shaped transducer usable in the present invention.

In the foregoing embodiment, an example has been described wherein an electronic scanning type array transducer being complicated in configuration but considered to be excellent for general purpose use is employed as the ultrasonic transducer; but the application range of the present invention is not limited thereto and may also be applied to a single focus manual scanning type transducer or a single focus mechanical scanning type transducer, an example of which is shown in sectional form in FIG. 18, and a non-focus type plane wave transducer an example of which is shown in sectional form in FIG. 19. In the FIGS. 18 and 19, an electrode 73 is connected to a coaxial connector 76 by a lead wire 75. A housing 77 made of a metal of high thermal conductivity such as copper or aluminum is provided with a water conduit 78 for cooling to deprive heat generated by the piezoelectric device during ultrasound generating operation or, if necessary, to cool an object irradiated with ultrasonic waves. In FIG. 18, the thickness of the central part of an acoustic lens 80 made of magnesium or a magnesium-based alloy is set to be ¼ or ½ wavelength of the fundamental frequency, thus insuring high efficiency. In FIG. 19, the thickness of a flat plate 79 made of light metal such as magnesium or aluminum is set to be ¼ or ½ wavelength of the fundamental frequency, thus insuring high efficiency.

Conventionally, in the case of the plane wave for which a high ultrasonic intensity level is hardly obtained, it was in effect impossible to generate cavitation sufficient for practical use in a non-stationary acoustic field, but the second harmonic wave superimposing method of the present invention succeeds in making the generation of cavitation possible. Through this, even when a plane wave transducer as shown in FIG. 19 is applied on the surface of the body or used during an operation, therapeutic effects can be obtained. Further, even by implanting a needle-shaped transducer, an example of which is shown in sectional form in FIG. 20, in an affected part, therapeutic effects can be obtained. In this case, the configuration is such that ultrasound is somewhat diffused by a tip conical part 81 made of magnesium or a magnesium-based alloy. When the ultrasound is desired to be prevented from being diffused, the tip conical part 81 may be made of a material exhibiting a relatively slow sound speed.

In the foregoing, the embodiments have been described which make the generation of cavitation efficient by superimposing on the fundamental wave the second harmonic wave thereof, but more efficient generation of cavitation can also be attained by superimposing a wave having a fourth, sixth or eighth harmonic of the fundamental wave on the aforementioned waves.

Next, other embodiments of the present invention will be described in greater detail with reference to FIGS. 21 to 24.

These embodiments, although the embodiment of FIG. 19 is similar in this point, make use of the fact that phase rotation due to the diffraction effect can be neglected in near acoustic fields of plane waves and therefore if plane waves of the two frequency waves are added to each other in the respective near acoustic fields so that wave fronts of the two frequency waves may become parallel to each other, then the phase relation between the two frequency waves can be conditioned to be advantageous to the generation of acoustic cavitation over a wide region.

Figure 21:
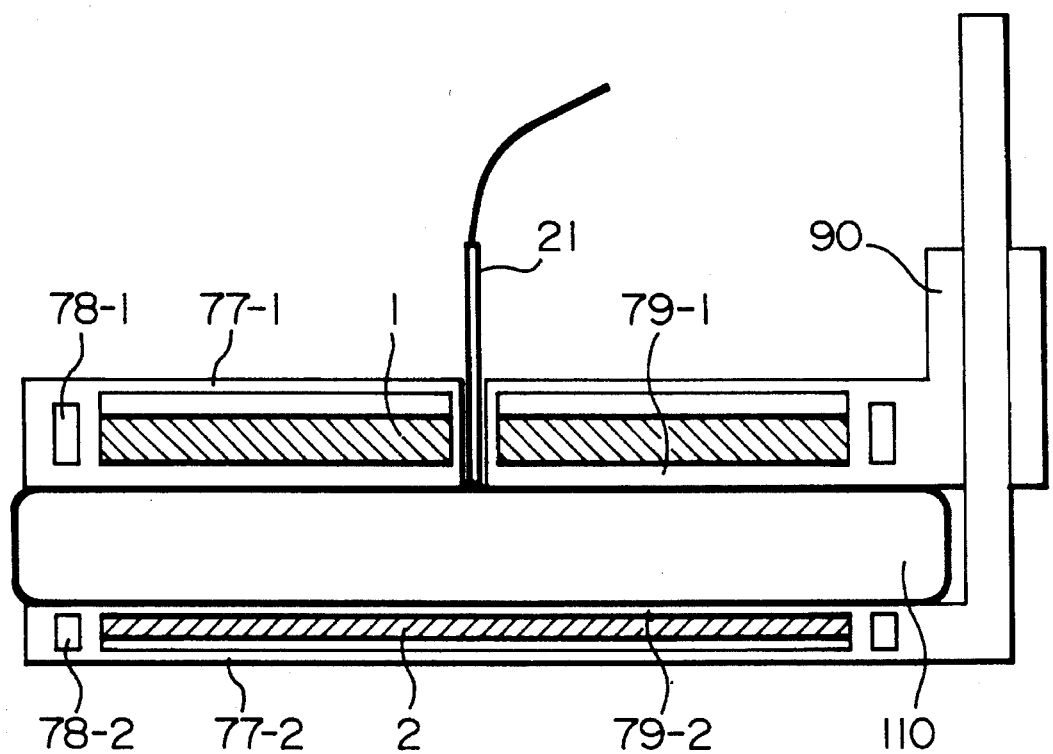
FIG. 21 is a diagram showing an example of the configuration of an intraoperative therapeutic ultrasound transducer according to the present invention.

In connection with an ultrasonic therapeutic apparatus representing an embodiment of the present invention, an example of the configuration of an intraoperative ultrasonic therapeutic transducer unit is shown in FIG. 21. Planar piezoelectric devices 1 and 2 for generating the fundamental wave and the second harmonic wave, respectively, are mounted so as oppose to each other in parallel. The two piezoelectric devices are respectively bonded to acoustic matching layers 79-1 and 79-2 each made of a magnesium-based alloy with sufficient acoustic strength. Heat generated during the generation of ultrasonic waves is led from the acoustic matching layers of high thermal conductivity to housings 77-1 and 77-2 each made of metal of high thermal conductivity and is removed from the transducer unit through water conduits 78-1 and 78-2 for cooling. If necessary, this cooling function can also be used for the purpose of cooling the vicinity of the surface of an affected part representing an object to be irradiated with ultrasound.

For example, when an affected part at a lobule 110 of the liver is treated, the affected part is irradiated with ultrasonic waves of the fundamental frequency and second harmonic simultaneously from the both sides of the affected part while being sandwiched in between the planar piezoelectric devices 1 and 2. The distance between the planar piezoelectric devices 1 and 2 can be adjusted by means of a parallel moving mechanism 90 which keeps the planar piezoelectric devices 1 and 2 parallel to each other. The distance between the surfaces of the acoustic matching layers 79-1 and 79-2 of the two piezoelectric devices is set in principle to be an integer multiple of a half wavelength of the fundamental wave. A space between each of the two acoustic matching layers and the lobule 110 of the liver may be filled, as necessary, with a jelly having the same osmotic pressure as the living body to assist transmission of the ultrasound. A compact ultrasonic detector 21 is mounted in a small hole formed in a central portion of, for example, the planar 1 piezoelectric device to detect higher harmonics and higher harmonics of subharmonics, these harmonics being generated in correspondence to the generation of acoustic cavitation. Based on detected signals, the irradiation intensity of the fundamental wave and the second harmonic wave is adjusted or the aforementioned distance between the surfaces of the acoustic matching layers 79-1 and 79-2 is adjusted finely for the purpose of attaining optimization.

Figure 22:
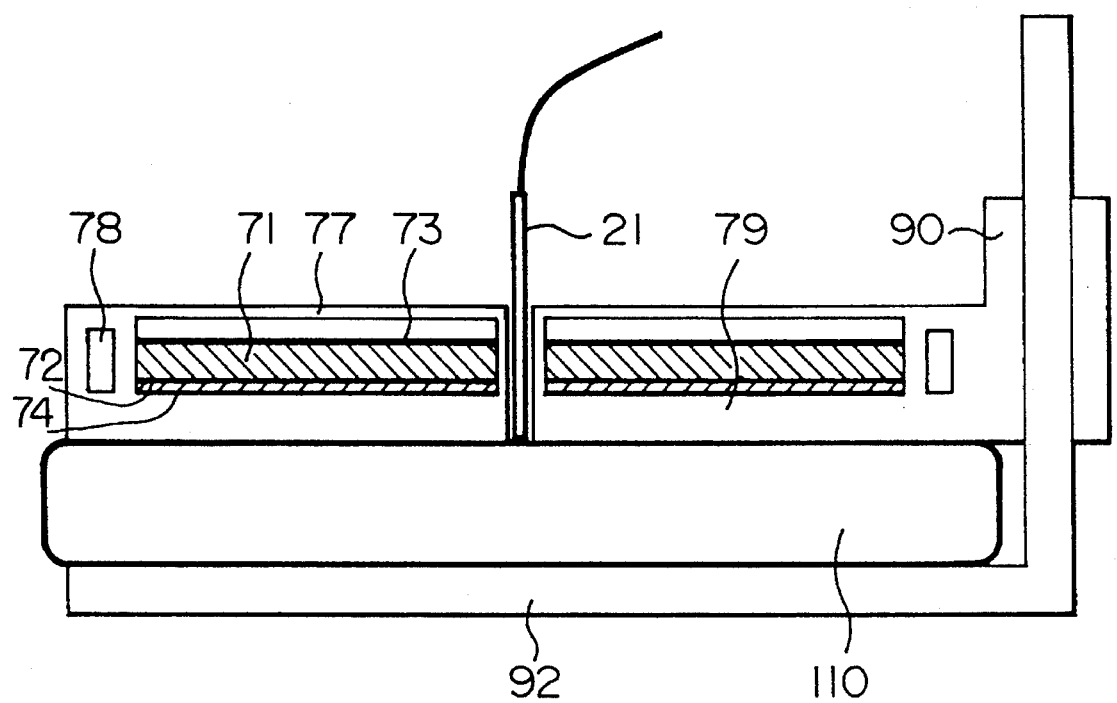
FIG. 22 is a diagram showing another example of the configuration of the intraoperative therapeutic ultrasound transducer according to the present invention.

FIG. 22 shows an example of an intraoperative ultrasonic therapeutic transducer unit configured to generate the fundamental wave and the second harmonic wave simultaneously from a single piezoelectric device in contrast to FIG. 21.

A reflection plate 92 made of, for example, stainless steel and having a thickness of an integer multiple of a half wavelength of the fundamental frequency wave is mounted to oppose a planar piezoelectric device for simultaneous generation of the fundamental wave and the second harmonic wave (the combination of 71 and 72 having the same configuration as that explained in connection with FIG. 8) in parallel thereto. The planar piezoelectric device is bonded to a thickness mode vibrator element plate 79 made of a magnesium-based or aluminum-based alloy and having a thickness of an integer multiple of the half wavelength of the fundamental wave, with sufficient acoustic strength. For example, when an affected part at a lobule 110 of the liver is treated, the affected part is irradiated with ultrasonic waves of the fundamental frequency and second harmonic simultaneously from the planar piezoelectric device while placing the affected part between the planar piezoelectric device and the reflection plate 92. The distance between the planar piezoelectric device and the reflection plate 92 can be adjusted by means of a parallel moving mechanism 90 which keeps the planar piezoelectric device and the reflection plate 92 parallel to each other. The distance between the surfaces of the thickness mode vibrator element plate 79 and reflection plate 92 is set for optimization similarly to the aforementioned distance between the surfaces of 79-1 and shown in FIG. 21.

With this configuration, acoustic fields substantially equal to the stationary acoustic fields set up between the two planar piezoelectric devices 1 and 2 and the two acoustic matching layers 79-1 and 79-2 in the embodiment of FIG. 21 can be formed between the thickness mode vibrator element plate 79 and the reflection plate 92. Since the reflection plate 92 can be designed to be much thinner than the housing 79-2 of planar piezoelectric device 2, this embodiment is superior in the point of ease of intraoperative use and in this respect the configuration of FIG. 22 is more advantageous than the configuration of FIG. 21.

The intraoperative ultrasonic therapeutic transducer shown in FIG. 21 or 22 can each replace the transducer elements 1—1 to 1-N and 2-1 to 2-M or the transducer elements 1—1 to 1-N in the configuration of the ultrasonic therapeutic apparatus of the embodiment shown in FIG. 3 or 7 to constitute an intraoperative ultrasonic therapeutic apparatus. The ultrasonic detector 21 in FIG. 21 or 22 corresponds to the probe 21 in FIG. 3 or 7.

FIG. 23 shows an example of the configuration of a reactor of an ultrasonic chemical reaction apparatus according to an embodiment of the present invention. A reaction vessel 91 is filled with liquid, reactants or substances for a sono-chemical reaction dissolved or scattered in the liquid are caused to flow into the reaction vessel 91 through an inlet 93, and a product stemming from a sono-chemical reaction, also dissolved or scattered in the liquid, is caused to flow out of the reaction vessel 91 through an outlet 94. When mutually parallel acoustic matching layers 79-1 and 79-2 constituting part of the inner wall of the reaction vessel 91 are made of magnesium-based light metal as in the embodiment of FIG. 21, each layer has a thickness of ¼ wavelength of the corresponding wave or the sum of a ¼ wavelength of the corresponding wave and a half wavelength of the corresponding wave. However, when the layers are made of stainless steel or quartz glass with the aim of ensuring a required chemical stability, each layer has a thickness of an integer multiple of the half of the corresponding wave. The distance between inner walls of the reaction vessel is set to an integer multiple of the half wavelength of the fundamental wave so as to meet the resonance condition. The illustrated example was designed so that this distance was selected to be one wavelength of the fundamental wave in order to allow anti-nodes of stationary wave acoustic pressure to occur not only in the vicinity of the inner wall but also in a central portion of the vessel for both the fundamental wave and the second harmonic wave. The configuration of FIG. 23 which is essentially superior in point of the generation of acoustic cavitation is also advantageous to the configuration of a bubble generator.

FIG. 24 shows an example of the configuration of a reactor of an ultrasonic chemical reaction apparatus or a bubble generator in which the fundamental wave and the second harmonic wave are generated from a single piezoelectric device at the same time. A planar piezoelectric device capable of generating the fundamental wave and the second harmonic wave simultaneously is bonded, with sufficient acoustic strength, to a thickness made vibrator element plate 79 which is made of stainless steel or quartz glass, has a thickness of an integer multiple of a half wavelength of the fundamental wave and forms part of the outer wall of a reaction vessel 91. An outer wall 92 opposing the thickness mode vibrator element plate 79 in parallel thereto has a thickness which is also an integer multiple of the half wavelength of the fundamental wave and serves as a reflection plate. With this configuration, acoustic fields essentially equal to the stationary acoustic fields set up between the two acoustic matching layers 79-1 and 79-2 in the embodiment of FIG. 23 can be formed between the thickness mode vibrator element plate 79 and the reflection plate 92.

Figure 25:
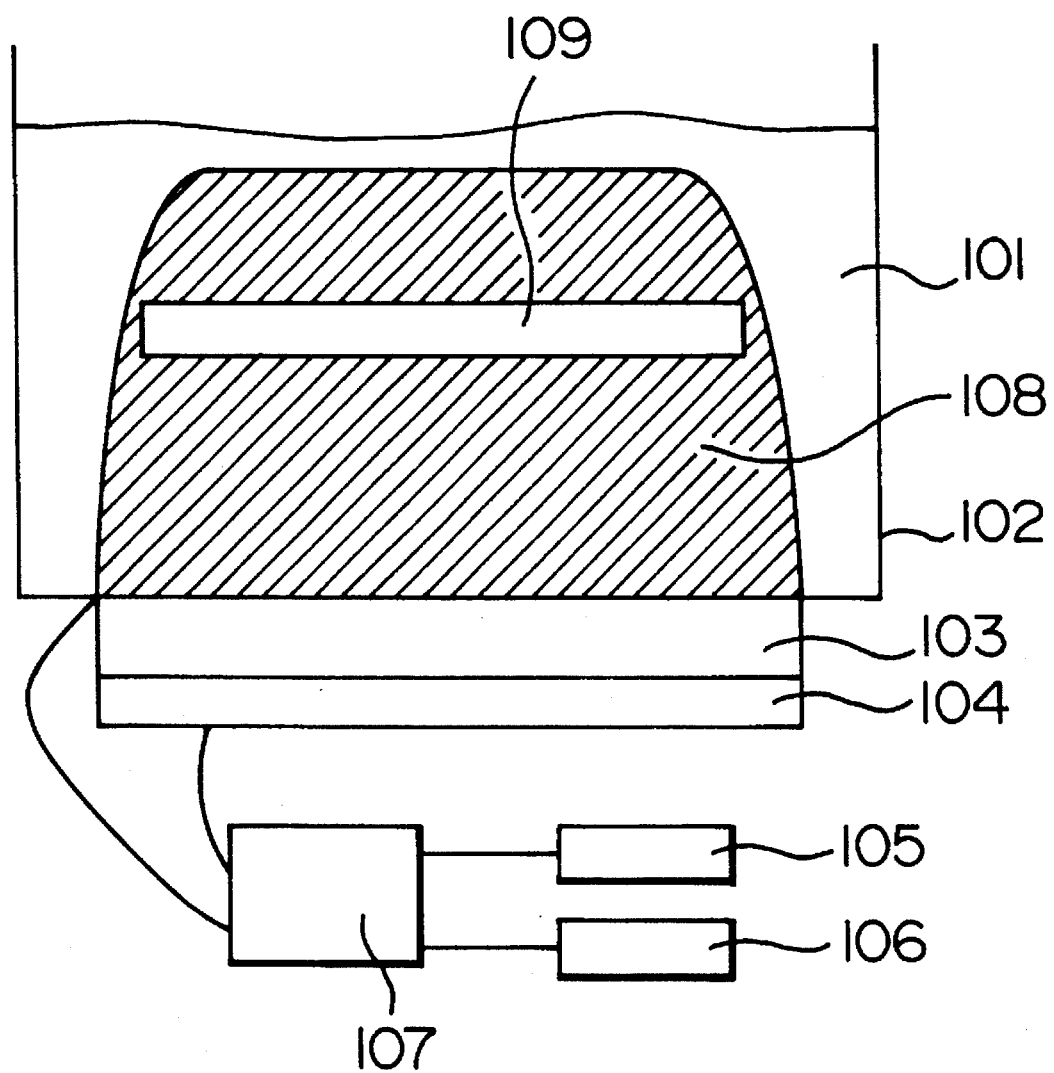
FIG. 25 is a diagram showing an example of the configuration of an ultrasonic cleaning apparatus according to the present invention.

Next, an embodiment of a cleaning apparatus for performing cleaning in a cleaning tank by irradiating the fundamental and the second harmonic wave will be described with reference to FIG. 25.

There are provided a cleaning tank 102 for containing a liquid 101, for example, a semiconductor substrate cleaning liquid containing pure water or hydrogen peroxide and ammonia, a piezoelectric device 103 having its vibrator element surface bonded to the bottom of the cleaning tank 102, a flat plate 104 which is bonded to the piezoelectric device 103, is made of a solid state material having substantially the same acoustic impedance as the piezoelectric device 103 and has an acoustic thickness in the vibration direction which is ½ of that of the 103, waveform generators 105 and 106 adapted to generate electrical signals of resonance frequencies $f_o$ and $2f_o$, respectively, of a complex resonant type thickness mode vibrator element constituted by 103 and 104, and an amplifier circuit 107 which adds together the electrical signals delivered out of the waveform generators 105 and 106 and amplifies them to apply AC voltages to the piezoelectric device 103. With this configuration, ultrasonic waves of frequencies $f_o$ and $2f_o$ are irradiated in the cleaning liquid 101 contained in the cleaning tank 102.

In the ultrasonic cleaning apparatus configured as above, the vibrator element constituted by the bonded piezoelectric device 103 and flat plate 104 has substantially the same configuration as the piezoelectric thickness mode vibrator element explained previously in connection with FIG. 8 and by performing excitation by means of the waveform generators 105 and 106 and the amplifier circuit 107, the fundamental wave $f_o$ and the second harmonic wave $2f_o$ can coexist in a region 108. When an object 109 to be washed, for example, a semiconductor substrate, is placed in this region 108, acoustic cavitation is generated highly efficiently at a surface of the object 109 to be washed and the surface of the object 109 to be washed can be washed by the acoustic cavitation.

Figure 26:
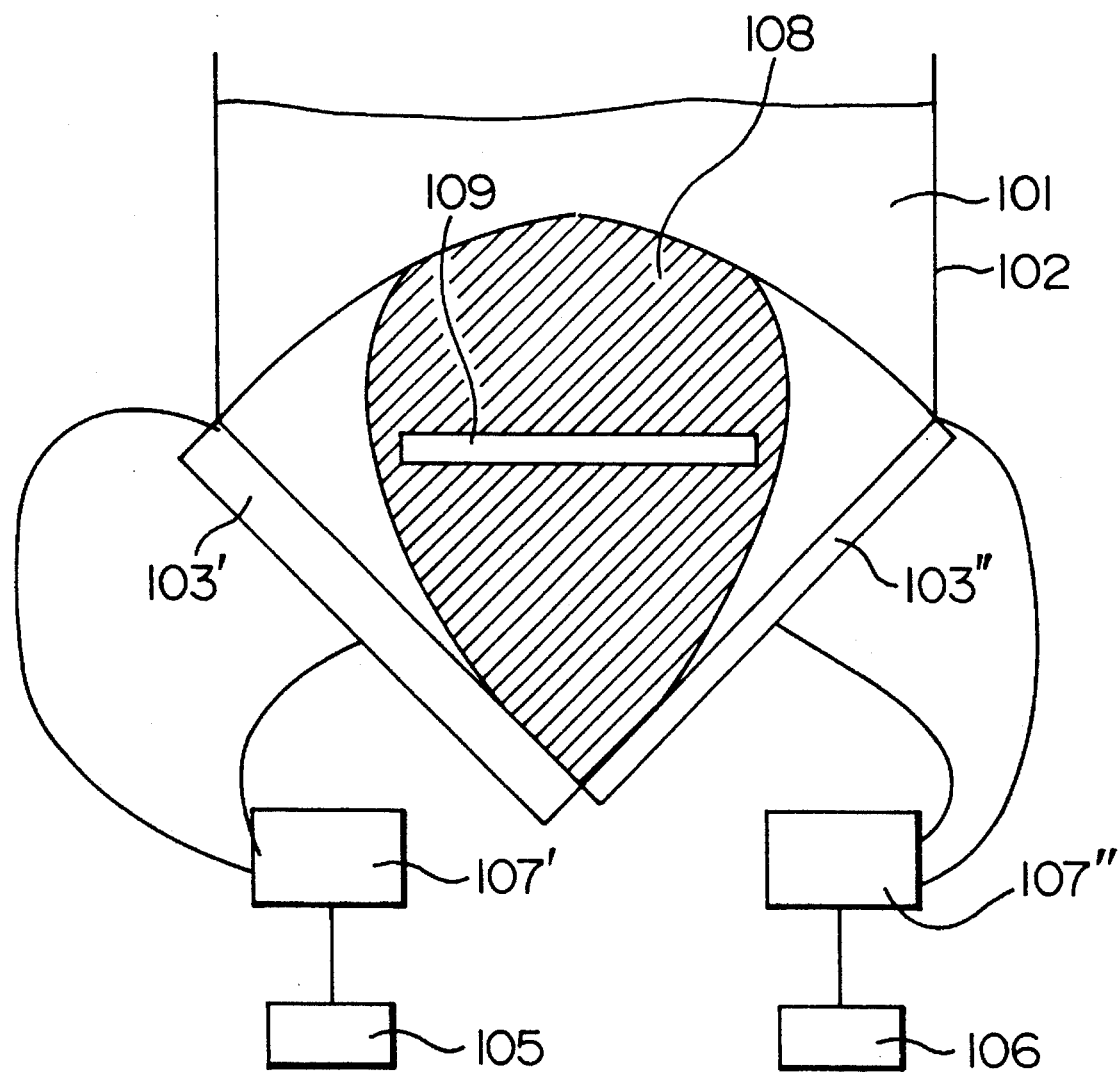
FIG. 26 is a diagram showing another example of the configuration of the ultrasonic cleaning apparatus according to the present invention.

Next, an embodiment of a cleaning apparatus for performing cleaning in a cleaning tank by irradiating the fundamental wave and the second harmonic wave from different vibrator elements will be described with reference to FIG. 26.

There are provided a cleaning tank 102 for containing a liquid 101 for cleaning, a piezoelectric device 103' having its vibrator element surface bonded to one of bottom surfaces of the cleaning tank and being resonant at a fundamental frequency $f_o$ and a piezoelectric device 103" disposed on the other bottom surface of the cleaning tank and being resonant at a second harmonic wave $2f_o$ of the $f_o$; and a waveform generator 105 for generating an electrical signal having a component of the frequency $f_o$ and a waveform generator 106 for generating an electrical signal having a component of the frequency $2f_o$ which are amplified by amplifiers 107' and 107", respectively, and applied to the piezoelectric devices 103" and 103" to vibrate them, thereby irradiating ultrasonic waves in the liquid 101 for cleaning. As a result, the fundamental wave $f_o$ and its second harmonic wave $2f_o$ can coexist in a region 108. When an object 109 to be washed, for example, a semiconductor substrate, is placed in this region, acoustic cavitation is generated highly efficiently at the surface of the object 109 to be washed and the surface of the object 109 to be washed can be washed by the acoustic cavitation.

Figure 27:
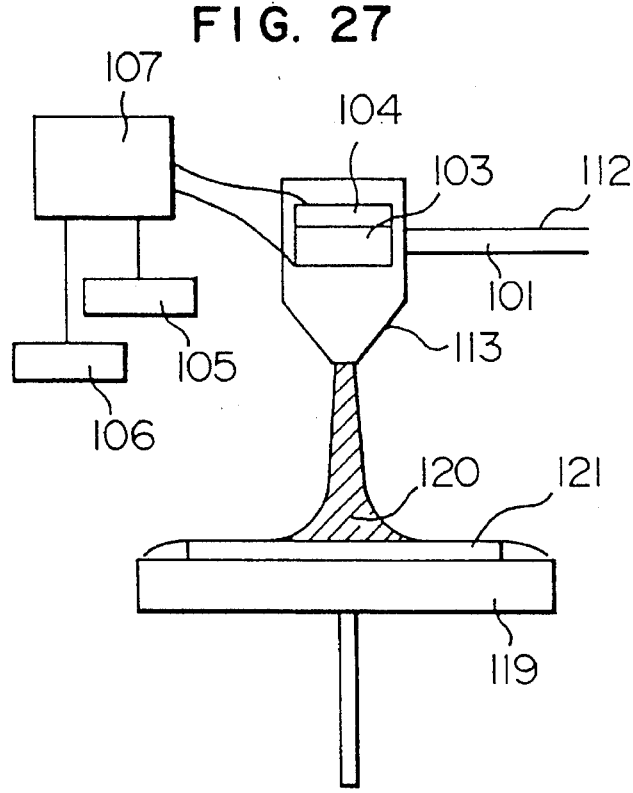
FIG. 27 is a diagram showing still another example of the configuration of the ultrasonic cleaning apparatus according to the present invention.

Next, an embodiment of a cleaning apparatus for performing cleaning by irradiating ultrasonic waves in a cleaning liquid jetted out of a jetting unit will be described with reference to FIG. 27.

This embodiment comprises a pipe 112 for guiding a liquid 101 for cleaning, for example, pure water, a nozzle 113 attached to the tip of the pipe, a piezoelectric device 103 held inside the nozzle 113, a flat plate 104 which is made of a solid having approximately the same acoustic impedance as the piezoelectric device 103 and has an acoustic thickness in the vibrator element direction which is ½ of that of the piezoelectric device 103, waveform generators 105 and 106 for generating signals of resonance frequencies $f_o$ and $2f_o$, respectively, of a complex thickness mode vibrator element constituted by 103 and 104, and an amplifier circuit 107 by which signals delivered out of the waveform generators 105 and 106 are added together and amplified so as to be applied to the piezoelectric device 103.

In the ultrasonic cleaning apparatus configured as above, the vibrator element constituted by the bonded piezoelectric device 103 and flat plate 104 has essentially the same configuration as the piezoelectric thickness vibrator made element explained previously in connection with FIG. 8 and when excitation is carried out by means of the waveform generators 105 and 106 and amplifier circuit 107, the fundamental wave $f_o$ and its second harmonic wave $2f_o$ can coexist in a region 120 of the cleaning liquid 101 jetted out of the nozzle 113. When the cleaning liquid 101 is emitted from the nozzle 113 toward a rotating or stationary stage 119, there results highly efficient generation of acoustic cavitation at the surface of an object 121 to be washed, for example, a semiconductor substrate, within the region 120 and the surface of the object 121 to be washed can be washed by this acoustic cavitation.

Results from evaluation of chemical cleaning effects brought about by the embodiments of the ultrasonic cleaning apparatus of FIGS. 25 to 27, especially of FIG. 25, will be described.

As an example of chemical cleaning, a semiconductor substrate was washed through oxidation by using ammonia and hydrogen peroxide. Since the progress of oxidation in the semiconductor substrate stopped as it reached a constant depth and was difficult to quantify, a substance exhibiting a color reaction due to oxidation was disposed at a position in a cleaning container where the semiconductor was disposed and the rate of oxidation of the substance due to irradiation of the ultrasonic waves was measured so as to be used as an index of efficiency of cleaning. Experiments were conducted with respect to a reaction in which triiodide ions $I_3^-$ were generated from iodine ions $2I^-$ through oxidization. An aqueous solution in which potassium iodide chloral hydrate were dissolved was disposed in a bag made of polyethylene and having a thickness of 0.03 mm, and the bag was disposed at the semiconductor holding position and irradiated with the ultrasonic waves. Concentration of the generated triiodide ions was determined by absorbance and the oxidation rate was determined from a value of the absorbance. The oxidation rate obtained when a fundamental wave at 750 kHz and a second harmonic wave at 1.5 MHz were irradiated simultaneously while the sum of power levels of the two ultrasonic waves was maintained constant was plotted relative to the ratio of the power at the fundamental frequency to the total ultrasonic power to obtain the oxidation rate which had the same characteristics as those explained previously in connection with FIG. 6. In this case, the sum of ultrasonic intensity levels of the fundamental wave and the second harmonic wave at the location where the oxidation occurred was about 30 W/cm². With the fundamental wave or the second harmonic wave alone used, the oxidation rate was zero within the experimental error range but the synergistic effects obtained when the two frequency waves were irradiated at the same time were remarkable and especially when the ratio of the power at the fundamental frequency to the total ultrasonic power was 0.2 to 0.8 (fundamental wave: second harmonic wave=1:4 to 4:1), a high oxidation rate was obtained.

Figure 28:
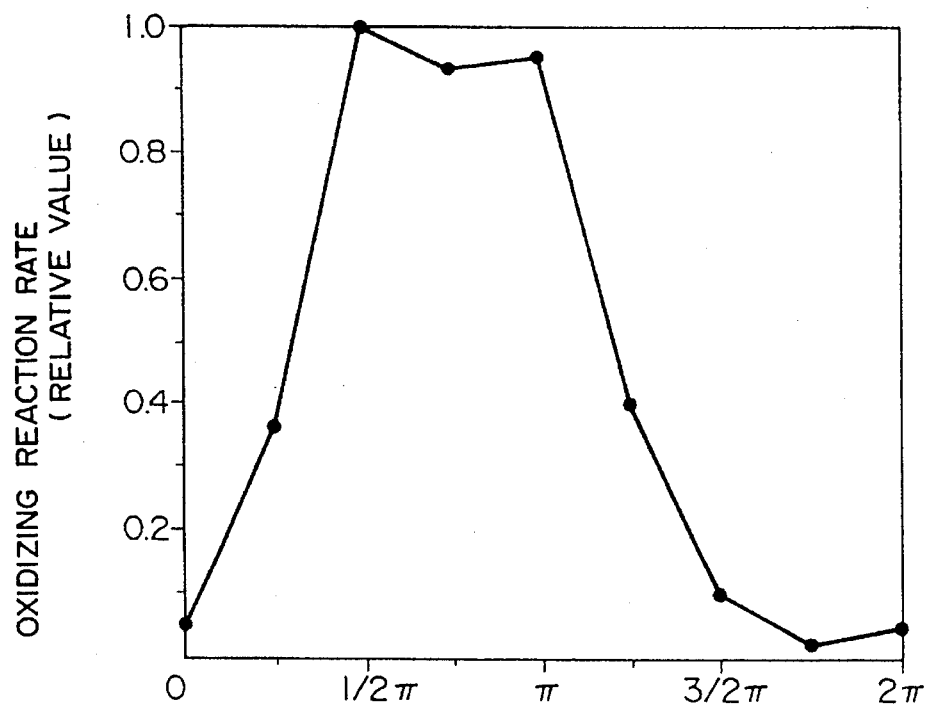
FIG. 28 is a diagram showing experimental results of oxidation induced by ultrasonic irradiation while changing a phase relation between the fundamental wave and the second harmonic wave which are superimposed on each other.

When the acoustic power ratio between the fundamental wave and the second harmonic wave is fixed to 1:1 and the phase relation between the fundamental wave and the second harmonic wave is changed, the oxidation rate is plotted to obtain results as shown in FIG. 28. In this case, too, the sum of ultrasonic intensity levels of the fundamental wave and second harmonic wave at a location where oxidation occurred was about 30 W/cm². In FIG. 28, the abscissa represents values of $\alpha$ when letting the fundamental wave be $\sin(2\pi f)$ and the second harmonic wave be $\sin(4\pi f + \alpha)$. When the value of $\alpha$ was being $(¼)\pi$ to $(⅞)\pi$, a high oxidation rate was obtained. Especially for $\pi/2 \leq \alpha \leq \pi$, a remarkably high oxidation rate was obtained, where $\alpha = \pi/2$ is a phase relation which maximizes the absolute value of negative peak acoustic pressure and $\alpha = \pi$ is a phase relation which makes the fall of acoustic pressure steepest.

The ultrasonic cleaning apparatus of the present embodiment was also effective for cleaning using hydrogen peroxide and sulfuric acid, cleaning using trichloroacetic acid and cleaning using chloral hydrate.

Next, an example in which the present invention is applied to sterilization of liquid will be described with reference to FIG. 29.

The present embodiment comprises a processing tank 201, a liquid filling port 202, a liquid discharge port 203, valves 204, a bubble injection port 205, a piezoelectric device 206 having its vibrator element surface bonded to the bottom of the processing tank 201, a flat plate 207 which is bonded to the piezoelectric device 206, has substantially the same acoustic impedance as the piezoelectric device 206 and is made of a solid having the same acoustic impedance as piezoelectric device the 206 and an acoustic thickness in the vibrator element direction measuring ½ of that of the piezoelectric device 206, waveform generators 208a and 208b for generating electrical signals of resonance frequencies $f_o$ and $2f_o$ of a complex resonance thickness made vibrator element constituted by 206 and 207, and an amplifier circuit 209 for adding together and amplifying electrical signals delivered out of the waveform generators 208a and 208b.

Here, the relation between the piezoelectric device 206 and flat plate 207 is defined similarly to the embodiment of FIG. 25 as described in connection with FIG. 8. When AC voltages of the resonance frequencies $f_o$ and $2f_o$ are applied to the piezoelectric device 206 to excite it and ultrasonic waves are irradiated in the liquid in the processing tank 201, the fundamental wave $f_o$ and its second harmonic wave $2f_o$ can coexist in the liquid in the processing tank. Through this, acoustic cavitation is generated efficiently in the processing tank and sterilization of the liquid can be carried out.

At that time, if gas such as air is injected from the bubble injection port 205, then a caviation core is allowed to exist stably and the effect of sterilization will be less degraded even when the ultrasonic waves are irradiated for a long time. By adjusting the degree of opening of the valves 204 and a timing therefor, the throughput and processing time of the liquid can be changed.

In the case where the composition of the liquid is allowed to be changed, the sterilization effect per hour can be improved by adding to the liquid a sono-chemical activation substance including a dye in the porphyrin family such as hematoporphyrin or chlorin or a haloid compound such as chloral hydrate or tetrachloroacetic acid.

Figure 30:
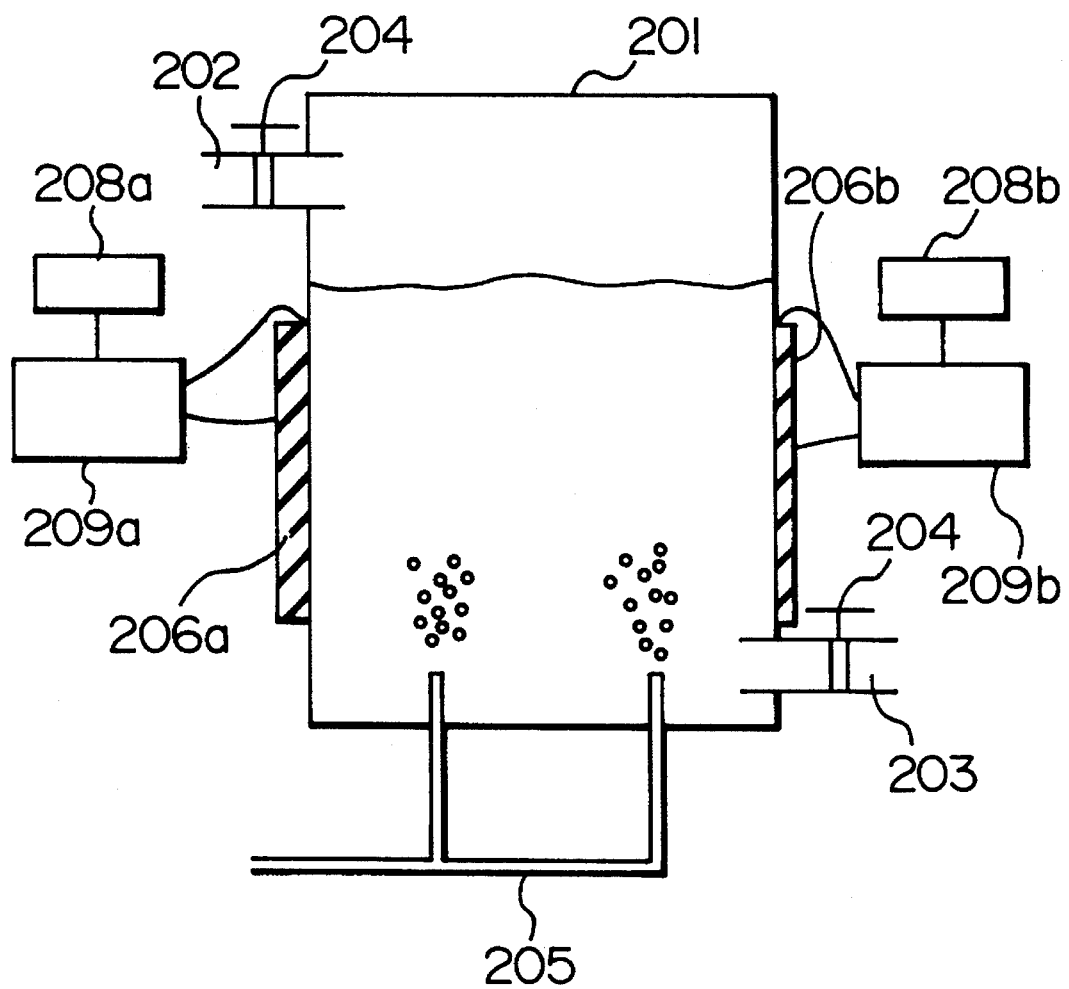
FIG. 30 is a diagram showing another example of the configuration of the sterilizing apparatus according to the present invention.

Like the embodiment of FIG. 26, a processing apparatus for performing sterilization in a processing tank by irradiating the fundamental wave and the second harmonic wave from different locations can be provided and an embodiment to this effect will be described with reference to FIG. 30.

Figure 29:
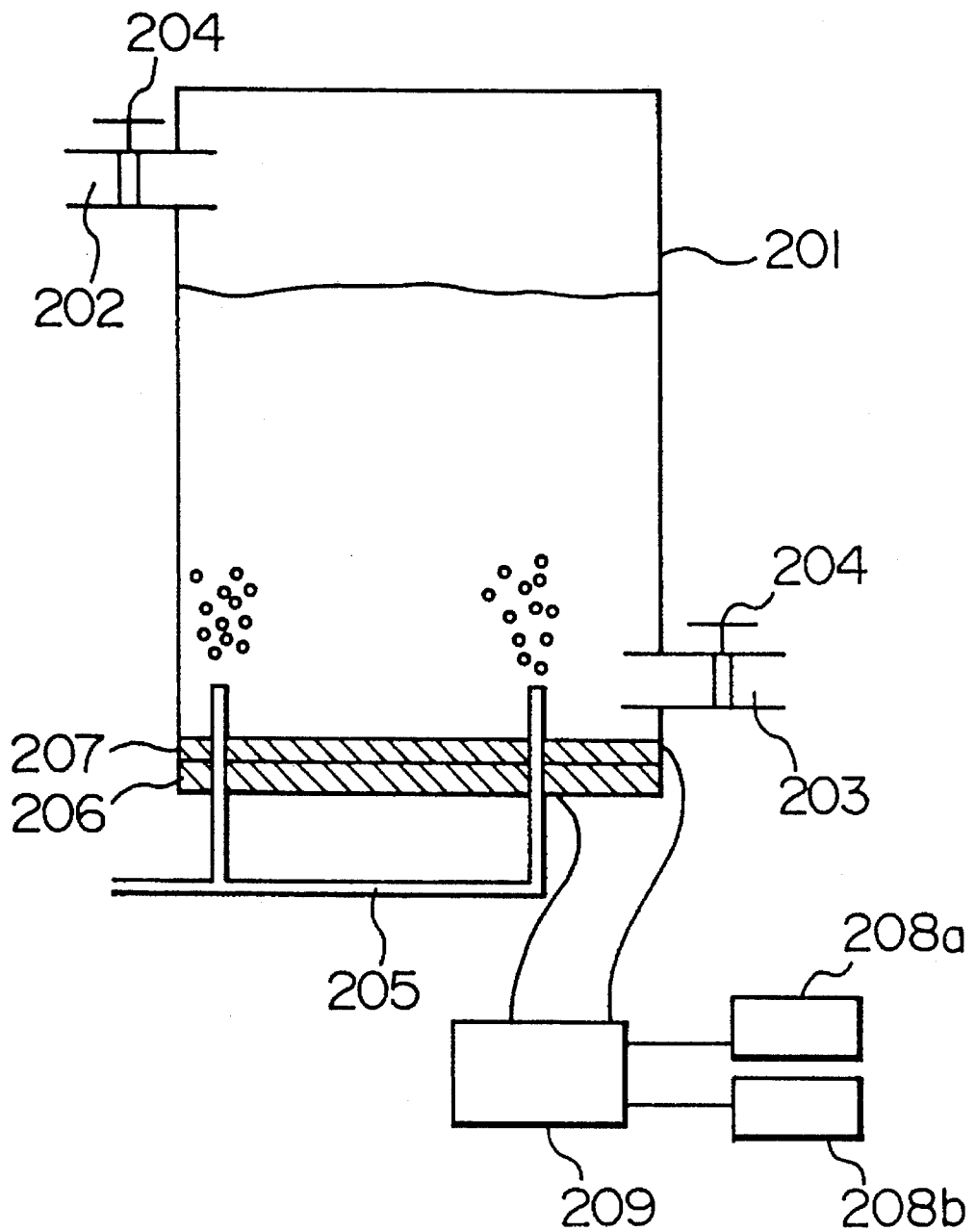
FIG. 29 is a diagram showing an example of the configuration of a sterilizing apparatus according to the present invention.

The overall configuration of a liquid processing apparatus is similar to FIG. 29 and differs therefrom only in that vibrator element surfaces of an ultrasonic vibrator element 206a resonant with a fundamental frequency $f_o$ and an ultrasonic vibrator element 206b resonant with a second harmonic wave $2f_o$ are independently bonded to opposite side walls of a processing tank 201, and electrical signals delivered out of a waveform generator 208a for generating an electrical signal having a component of the fundamental frequency $f_o$ and a waveform generator 208b for generating an electrical signal having a component of the second harmonic of $f_o$ are independently amplified by amplifiers 209a and 209b, respectively, to apply AC voltages to the ultrasonic vibrator elements 206a and 206b.

When ultrasonic waves are irradiated into the processing tank 201 by means of the ultrasonic vibrator elements 206a and 206b, the fundamental wave $f_o$ and its second harmonic wave $2f_o$ are allowed to coexist in the processing tank. Through this, acoustic cavitation occurs efficiently in the processing tank and sterilization of the liquid can be carried out.

We claim:

1. An apparatus for irradiating an object with a plurality of ultrasonic waves having mutually different frequencies, comprising:

first generating means for generating a fundamental ultrasonic wave having a fundamental frequency $f_o$;

second generating means for generating a second harmonic ultrasonic wave having a second harmonic frequency $2f_o$;

driving means for driving the first generating means with a first electric signal for causing the first generating means to generate the fundamental ultrasonic wave substantially continuously, and for driving the second generating means with a second electric signal for causing the second generating means to generate the second harmonic ultrasonic wave substantially continuously; and irradiating means for substantially simultaneously irradiating an object with the fundamental ultrasonic wave and the second harmonic ultrasonic wave so as to generate ultrasonic cavitation in the object or in a vicinity of the object by virtue of a synergistic effect occurring between the fundamental ultrasonic wave and the second harmonic ultrasonic wave.

2. An apparatus according to claim 1, wherein the first generating means and the second generating means are independent of one another; and wherein a frequency of the first electric signal is the fundamental frequency $f_o$, and a frequency of the second electric signal is the second harmonic frequency $2f_o$.

3. An apparatus according to claim 2, wherein the first generating means and the second generating means have a common focal point; and wherein the object is disposed at the common focal point of the first generating means and the second generating means.

4. An apparatus according to claim 2, wherein the first generating means includes a first array of transducer elements for generating the fundamental ultrasonic wave, and the second generating means includes a second array of transducer elements for generating the second harmonic ultrasonic wave.

5. An apparatus according to claim 1, wherein the first generating means generates the fundamental ultrasonic wave and the second generating means generates the second harmonic ultrasonic wave such that an intensity of the second harmonic ultrasonic wave at the object is greater than ¼ times and less than 4 times an intensity of the fundamental ultrasonic wave at the object.

6. An apparatus according to claim 1, wherein the first generating means generates the fundamental ultrasonic wave and the second generating means generates the second harmonic ultrasonic wave such that a phase relation between the fundamental ultrasonic wave and the second harmonic ultrasonic wave at the object is such that a waveform of the second harmonic ultrasonic wave at the object approximates $-\sin(4\pi f_o t)$ with respect to time t when a waveform of the fundamental ultrasonic wave at the object is represented by $\sin(2\pi f_o t)$.

7. An apparatus according to claim 1, further comprising an ultrasonic imaging unit for forming an ultrasonic echo image of the object, the ultrasonic imaging unit transmitting and receiving an ultrasonic wave having a frequency higher than the second harmonic frequency $2f_o$.

8. An apparatus according to claim 7, wherein the fundamental ultrasonic wave and the second harmonic ultrasonic wave cause ultrasonic waves having frequencies which are even multiples of the second harmonic frequency $f_o$ to be generated at the object; and wherein the ultrasonic imaging unit receives the ultrasonic waves having frequencies which are even multiples of the second harmonic frequency $f_o$.

9. An apparatus for irradiating an object with a plurality of ultrasonic waves having mutually different frequencies, comprising:

generating means for generating a fundamental ultrasonic wave having a fundamental frequency $f_o$, and for generating a second harmonic ultrasonic wave having a second harmonic frequency $2f_o$;

driving means for driving the generating means with an electric signal for causing the generating means to generate the fundamental ultrasonic wave and the second harmonic ultrasonic wave substantially continuously; and irradiating means for substantially simultaneously irradiating an object with the fundamental ultrasonic wave and the second harmonic ultrasonic wave so as to generate ultrasonic cavitation in the object or in a vicinity of the object by virtue of a synergistic effect occurring between the fundamental ultrasonic wave and the second harmonic ultrasonic wave.

10. An apparatus according to claim 9, wherein the generating means includes a piezoelectric thickness mode vibrator element including a piezoelectric material and a material having substantially a same acoustic impedance as the piezoelectric material, the piezoelectric thickness mode vibrator element having an acoustic thickness of a half wavelength of the fundamental ultrasonic wave, and having a portion with an acoustic thickness of substantially ⅔ of the acoustic thickness of the piezoelectric thickness mode vibrator element which is driven piezoelectrically.

11. An apparatus according to claim 10, wherein the piezoelectric thickness mode vibrator element includes a layer of the piezoelectric material having an acoustic thickness of substantially ⅔ of the acoustic thickness of the piezoelectric thickness mode vibrator element, and a layer of the material having substantially the same acoustic impedance as the piezoelectric material having an acoustic thickness of substantially ⅓ of the acoustic thickness of the piezoelectric thickness mode vibrator element and being acoustically bonded to the layer of piezoelectric material; and wherein only the layer of the piezoelectric material having the acoustic thickness of substantially ⅔ of the acoustic thickness of the piezoelectric thickness mode vibrator element is driven piezoelectrically.

12. An apparatus according to claim 10, wherein the driving means includes:

a push-pull type switching circuit for driving the piezoelectric thickness mode vibrator element, the push-pull type switching circuit including a first switching element and a second switching element; and control means for controlling the first switching element to turn on and the second switching element to turn off in first periods, and for controlling the first switching element to turn off and the second switching element to turn on in second periods alternating with the first periods;

wherein a ratio of a duration of each of the first periods to a duration of each of the second periods is substantially 1:3 or 3:1.

13. An apparatus according to claim 10, wherein the driving means includes:

a first constant potential source;

a second constant potential source;

a third constant potential source;

a switching circuit for driving the piezoelectric thickness mode vibrator element, the switching circuit including
first switching means coupled between the first constant potential source and the piezoelectric thickness mode vibrator element,
second switching means coupled between the second constant potential source and the piezoelectric thickness mode vibrator element, and
third switching means coupled between the third constant potential source and the piezoelectric thickness mode vibrator element; and control means for controlling the first switching means, the second switching means, and the third switching means to turn on and off at predetermined timings.

14. An ultrasonic cleaning apparatus for ultrasonically cleaning an object with a plurality of ultrasonic waves having mutually different frequencies, comprising:

generating means for generating a fundamental ultrasonic wave having a fundamental frequency $f_o$, and for generating a second harmonic ultrasonic wave having a second harmonic frequency $2f_o$;

driving means for driving the generating means with at least one electric signal for causing the generating means to generate the fundamental ultrasonic wave and the second harmonic ultrasonic wave substantially continuously; and cleaning means for ultrasonically cleaning an object substantially simultaneously with the fundamental ultrasonic wave and the second harmonic ultrasonic wave.

15. An apparatus according to claim 14, further wherein the cleaning means includes:

a cleaning tank having the object disposed therein; and means for irradiating the object disposed in the cleaning tank substantially simultaneously with the fundamental ultrasonic wave and the second harmonic ultrasonic wave.

16. An apparatus according to claim 14, wherein the cleaning means includes:

a jetting unit for jetting a liquid onto the object; and means for irradiating the liquid substantially simultaneously with the fundamental ultrasonic wave and the second harmonic ultrasonic wave before the liquid is jetted onto the object.

17. An apparatus according to claim 14, wherein the generating means generates the fundamental ultrasonic wave and the second harmonic ultrasonic wave such that an intensity of the second harmonic ultrasonic wave at the object is greater than ¼ times and less than 4 times an intensity of the fundamental ultrasonic wave at the object.

18. An apparatus according to claim 14, wherein the generating means generates the fundamental ultrasonic wave and the second harmonic ultrasonic wave such that a phase relation $\alpha$ between the fundamental ultrasonic wave and the second harmonic ultrasonic wave at the object is such that a waveform of the second harmonic ultrasonic wave at the object approximates $\sin(4\pi f_o t+\alpha)$ with respect to time t when a waveform of the fundamental ultrasonic wave at the object is represented by $\sin(2\pi f_o t)$, where $\alpha$ is a real number which is greater than $(¼)\pi$ and less than $(7/4)\pi$.

19. An apparatus according to claim 14, wherein the generating means includes a piezoelectric thickness mode vibrator element, the piezoelectric thickness mode vibrator element including a layer of a piezoelectric material, and a layer of a material having substantially a same acoustic impedance as the piezoelectric material and being acoustically bonded to the layer of piezoelectric material.

20. An apparatus according to claim 19, wherein a ratio of a time defined by dividing a thickness of the layer of piezoelectric material in a vibration direction of the piezoelectric thickness mode vibrator element by a speed of sound in the piezoelectric material to a time defined by dividing a thickness of the layer of material having substantially the same acoustic impedance as the piezoelectric material in the vibration direction by a speed of sound in the material having substantially the same acoustic impedance as the piezoelectric material is greater than 1 and less than 3.

21. An ultrasonic liquid sterilizing apparatus for ultrasonically sterilizing a liquid with a plurality of ultrasonic waves having mutually different frequencies, comprising:

generating means for generating a fundamental ultrasonic wave having a fundamental frequency $f_o$, and for generating a second harmonic ultrasonic wave having a second harmonic frequency $2f_o$;

driving means for driving the generating means with at least one electric signal for causing the generating means to generate the fundamental ultrasonic wave and the second harmonic ultrasonic wave substantially continuously; and irradiating means for substantially simultaneously irradiating a liquid with the fundamental ultrasonic wave and the second harmonic ultrasonic wave so as to ultrasonically sterilize the liquid.

22. An apparatus according to claim 21, wherein the generating means includes a piezoelectric thickness mode vibrator element, the piezoelectric thickness mode vibrator element including a layer of a piezoelectric material, and a layer of a material having substantially a same acoustic impedance as the piezoelectric material and being acoustically bonded to the layer of piezoelectric material.

23. An apparatus according to claim 22, wherein a ratio of a time defined by dividing a thickness of the layer of piezoelectric material in a vibration direction of the piezoelectric thickness mode vibrator element by a speed of sound in the piezoelectric material to a time defined by dividing a thickness of the layer of material having substantially the same acoustic impedance as the piezoelectric material in the vibration direction by a speed of sound in the material having substantially the same acoustic impedance as the piezoelectric material is greater than 1 and less than 3.

24. An apparatus for irradiating an object with a plurality of ultrasonic waves having mutually different frequencies, comprising:

a piezoelectric vibrator element for generating a fundamental ultrasonic wave having a fundamental frequency $f_o$, and for generating a second harmonic ultrasonic wave having a second harmonic frequency $2f_o$;

a first driving circuit for driving the piezoelectric vibrator element such that the piezoelectric vibrator element generates the fundamental ultrasonic wave;

a second driving circuit for driving the piezoelectric vibrator element such that the piezoelectric vibrator element generates the second harmonic ultrasonic wave;

a first capacitance connected in parallel with the piezoelectric vibrator element, a total capacitance of the first capacitance and the piezoelectric vibrator element connected in parallel being C;

a first inductance having an inductance of $(5/8)L$ connected between the first driving circuit and the first capacitance and the piezoelectric vibrator element connected in parallel, L being a total inductance which is resonant with the total capacitance C at the fundamental frequency $f_o$; and a second inductance having an inductance of $(10/9)L$ and a second capacitance having a capacitance of $(9/25)C$ connected in series between the second driving circuit and the first capacitance and the piezoelectric vibrator element connected in parallel.

* * * * *